(12) United States Patent
Dunham et al.

(10) Patent No.: US 11,020,499 B2
(45) Date of Patent: Jun. 1, 2021

(54) DISINFECTION APPARATUS FOR A VEHICLE USING ULTRAVIOLET RADIATION

(71) Applicant: Ford Global Technologies, LLC, Dearborn, MI (US)

(72) Inventors: Scott Holmes Dunham, Redford, MI (US); Stuart C. Salter, White Lake, MI (US); Daniel Ferretti, Commerce Township, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 16/553,960

(22) Filed: Aug. 28, 2019

(65) Prior Publication Data

US 2021/0060191 A1    Mar. 4, 2021

(51) Int. Cl.
*A61L 2/10* (2006.01)
*B60R 15/00* (2006.01)

(52) U.S. Cl.
CPC ............... *A61L 2/10* (2013.01); *B60R 15/00* (2013.01); *A61L 2202/122* (2013.01); *A61L 2202/25* (2013.01)

(58) Field of Classification Search
CPC ........... A61L 2202/122; A61L 2202/25; A61L 2202/16; A61L 2/0047; A61L 2202/121
See application file for complete search history.

(56) References Cited

U.S. PATENT DOCUMENTS

| | | | |
|---|---|---|---|
| 4,830,154 A * | 5/1989 | Gerch | A45C 3/00 190/103 |
| 6,174,064 B1 * | 1/2001 | Kalantar | G02B 6/0036 362/23.15 |
| 6,908,597 B2 | 6/2005 | Chen et al. | |
| 8,816,636 B2 * | 8/2014 | Shinde | B60R 11/0235 320/108 |
| 9,124,109 B2 * | 9/2015 | Lota | H02J 7/0047 |
| 9,283,890 B1 * | 3/2016 | Huebner | B60R 7/04 |
| 9,339,571 B2 * | 5/2016 | Bilenko | A61L 2/10 |
| 9,592,312 B2 | 3/2017 | Lyslo et al. | |
| 10,376,605 B1 | 8/2019 | Majdali et al. | |

(Continued)

FOREIGN PATENT DOCUMENTS

| | | |
|---|---|---|
| CN | 2726973 Y | 9/2005 |
| DE | 102016215247 A1 | 2/2018 |

(Continued)

*Primary Examiner* — Brooke Purinton
(74) *Attorney, Agent, or Firm* — David Coppiellie; Price Heneveld LLP

(57) ABSTRACT

A vehicle comprising: a seating assembly; and a console disposed proximate the seating assembly. The console comprises a disinfection apparatus. The disinfection apparatus comprises a housing to accept items to be disinfected, and a source of ultraviolet radiation configured to emit ultraviolet radiation into the housing. In embodiments, the housing comprises a light guide operably coupled to at least one of a base and a lid, the light guide accepting the ultraviolet radiation from the source of the ultraviolet radiation and guiding the ultraviolet radiation within an interior chamber. In embodiments, the source of ultraviolet radiation is a light emitting diode configured to emit electromagnetic radiation having a peak intensity within a wavelength range of 200 nm to 300 nm.

20 Claims, 16 Drawing Sheets

(56) References Cited

U.S. PATENT DOCUMENTS

| | | |
|---|---|---|
| 2002/0098109 A1 | 7/2002 | Nelson et al. |
| 2007/0053188 A1 | 3/2007 | New et al. |
| 2007/0207066 A1 | 9/2007 | Thur et al. |
| 2008/0175761 A1 | 7/2008 | Thur et al. |
| 2010/0237649 A1 | 9/2010 | Concina |
| 2012/0062175 A1* | 3/2012 | Miller .................... H02J 50/40 320/108 |
| 2013/0063922 A1* | 3/2013 | La Porte .................. A61L 2/10 361/807 |
| 2014/0183377 A1* | 7/2014 | Bettles ..................... A61L 2/10 250/455.11 |
| 2014/0264076 A1* | 9/2014 | Bettles ..................... A61L 2/00 250/455.11 |
| 2015/0137747 A1* | 5/2015 | Salter ....................... B60N 3/14 320/108 |
| 2016/0000951 A1 | 1/2016 | Kreiner et al. |
| 2016/0074546 A1* | 3/2016 | Rizzone ................... A61L 2/26 250/455.11 |
| 2016/0089459 A1 | 3/2016 | Boodaghians et al. |
| 2016/0250362 A1 | 9/2016 | Mackin |
| 2017/0240263 A1* | 8/2017 | Kanazawa ............... B63J 4/002 |
| 2017/0313278 A1 | 11/2017 | Marew |
| 2018/0065126 A1 | 3/2018 | Abate et al. |
| 2019/0076558 A1 | 3/2019 | Zhang-Miske |
| 2020/0061223 A1* | 2/2020 | Hallack .................... A61L 2/28 |

FOREIGN PATENT DOCUMENTS

| | | | |
|---|---|---|---|
| DE | 102018002328 A1 | 9/2019 | |
| EP | 26678964 A1 | 12/2013 | |
| EP | 2668964 | * 12/2014 | ............ A61L 9/015 |
| JP | 2005130994 A | 5/2005 | |
| JP | 2011073617 A | 4/2011 | |
| KR | 0124687 Y1 | 6/1998 | |

\* cited by examiner

DISINFECTION APPARATUS FOR A VEHICLE USING ULTRAVIOLET RADIATION

FIELD OF THE INVENTION

The present invention generally relates to vehicle and, more specifically, to a disinfection apparatus for a vehicle.

BACKGROUND OF THE INVENTION

The inventors have identified a problem in that heretofore vehicles have not provided ways to disinfect items belonging to an occupant of the vehicle, such as smart phones, wallets, cosmetics, currency, pacifiers, and so on.

SUMMARY OF THE INVENTION

The present disclosure solves that problem with an in-vehicle disinfection apparatus that includes an interior chamber in which the occupant can place such items and an ultraviolet radiation source emitting ultraviolet radiation that irradiates upon, and thereby disinfects, those items.

According to a first aspect of the present invention, a disinfection apparatus for a vehicle comprises: a housing to accept items to be disinfected; and a source of ultraviolet radiation configured to emit ultraviolet radiation into the housing.

Embodiments of the first aspect of the invention can include any one or a combination of the following features:
  the housing comprises a base including an interior chamber;
  the housing comprises a lid operably connected to the base, the lid manipulable to, from, and between a closed position where the lid covers the interior chamber and an open position where the lid does not cover the interior chamber;
  the housing comprises a light guide operably coupled to at least one of the base and the lid, the light guide accepting the ultraviolet radiation from the source of the ultraviolet radiation and guiding the ultraviolet radiation within the interior chamber;
  the source of ultraviolet radiation is a light emitting diode configured to emit electromagnetic radiation having a peak intensity within a wavelength range of 200 nm to 300 nm;
  the light guide further comprises a contact surface open to the interior chamber and an opposite surface that faces in a generally opposite direction as the contact surface;
  the disinfection apparatus further comprises a reflective layer, disposed adjacent to the opposite surface of the light guide, that reflects at least 40 percent of incident electromagnetic radiation having a wavelength in a range of 200 nm to 300 nm;
  the disinfection apparatus further comprises a second light guide disposed at the other of the base and the lid, the second light guide comprising a contact surface that faces the contact surface of the light guide when the lid is in the closed position and an opposite surface that faces in a generally opposite direction as the contact surface of the second light guide, the second light guide accepting the ultraviolet radiation from the source of the ultraviolet radiation and guiding the ultraviolet radiation within the interior chamber when the lid is in the closed position;
  the light guide further comprises a first portion, a second portion, and a binding portion connecting the first portion and the second portion;
  the first portion comprises the contact surface;
  the second portion comprises another contact surface;
  the second portion has an open position relative to the first portion in which the contact surface of the second portion is separated from the contact of the first portion;
  the second portion has a closed position relative to the first portion in which the contact surface of the second portion is disposed adjacent the contact surface of the first portion;
  the light guide further comprises recesses extending into the contact surface or projections extending out of the contact surface;
  a compressive layer disposed between the base of the housing and the opposite surface of the light guide, the light guide being disposed at the base;
  a second compressive layer disposed between the lid of the housing and the opposite surface of the second light guide, the second light guide being disposed at the lid;
  the compressive layer and the second compressive layer compress the contact surface of the light guide against the contact surface of the second light guide, when the lid is in the closed position;
  the light guide is visually transparent such that an occupant can see through the light guide through the contact surface, through a thickness of the light guide, and through the opposite surface;
  the light guide is attached to the base, but a portion of the opposite surface of the light guide is separable from the base;
  the light guide further comprises a thickness that extends between the contact surface and the opposite surface; and
  the thickness of the light guide decreases as a function of the distance from where the light guide accepts the ultraviolet radiation from the source of the ultraviolet radiation.

According to a second aspect of the present invention, a vehicle comprises: a seating assembly; and a console disposed proximate the seating assembly. The console comprises a disinfection apparatus. The disinfection apparatus comprises a housing to accept items to be disinfected, and a source of ultraviolet radiation configured to emit ultraviolet radiation into the housing.

Embodiments of the second aspect of the invention can include any one or a combination of the following features:
  the housing comprises a base including an interior chamber;
  the housing comprises a lid operably connected to the base, the lid manipulable to, from, and between a closed position where the lid covers the interior chamber and an open position where the lid does not cover the interior chamber;
  the housing comprises a light guide operably coupled to at least one of the base and the lid, the light guide accepting the ultraviolet radiation from the source of the ultraviolet radiation and guiding the ultraviolet radiation within the interior chamber;
  the source of ultraviolet radiation is a light emitting diode configured to emit electromagnetic radiation having a peak intensity within a wavelength range of 200 nm to 300 nm;
  the light guide further comprises a contact surface open to the interior chamber and an opposite surface that faces in a generally opposite direction as the contact surface;

the disinfection apparatus further comprises a reflective layer, disposed adjacent to the opposite surface of the light guide, that reflects at least 40 percent of incident electromagnetic radiation having a wavelength in a range of 200 nm to 300 nm;

the disinfection apparatus further comprises a second light guide disposed at the other of the base and the lid, the second light guide comprising a contact surface that faces the contact surface of the light guide when the lid is in the closed position and an opposite surface that faces in a generally opposite direction as the contact surface of the second light guide, the second light guide accepting the ultraviolet radiation from the source of the ultraviolet radiation and guiding the ultraviolet radiation within the interior chamber when the lid is in the closed position;

the light guide further comprises a first portion, a second portion, and a binding portion connecting the first portion and the second portion;

the first portion comprises the contact surface;

the second portion comprises another contact surface;

the second portion has an open position relative to the first portion in which the contact surface of the second portion is separated from the contact surface of the first portion;

the second portion has a closed position relative to the first portion in which the contact surface of the second portion is disposed adjacent the contact surface of the first portion;

the disinfection apparatus further comprises a compressive layer disposed between the base of the housing and the opposite surface of the light guide, the light guide being disposed at the base, and the second light guide being disposed at the lid;

the disinfection apparatus further comprises a second compressive layer disposed between the lid of the housing and the opposite surface of the second light guide, the light guide being disposed at the base, and the second light guide being disposed at the lid;

the compressive layer and the second compressive layer compress the contact surface of the light guide against the contact surface of second light guide, when the lid is in the closed position;

the light guide is visually transparent such that an occupant can see through the light guide through the contact surface, through a thickness of the light guide, and through the opposite surface;

the light guide is attached to the base, but a portion of the opposite surface of the light guide is separable from the base;

the light guide further comprises a thickness that extends between the contact surface and the opposite surface; and the thickness of the light guide decreases as a function of a distance from where the light guide accepts the ultraviolet radiation from the source of the ultraviolet radiation.

According to a third aspect of the present invention, a method of disinfecting an item with a vehicle comprises activating a source of ultraviolet radiation to emit ultraviolet radiation into a housing of a disinfection apparatus to disinfect items disposed in the housing.

These and other aspects, objects, and features of the present invention will be understood and appreciated by those skilled in the art upon studying the following specification, claims, and appended drawings.

DETAILED DESCRIPTION OF THE PREFERRED EMBODIMENTS

Figure 1:
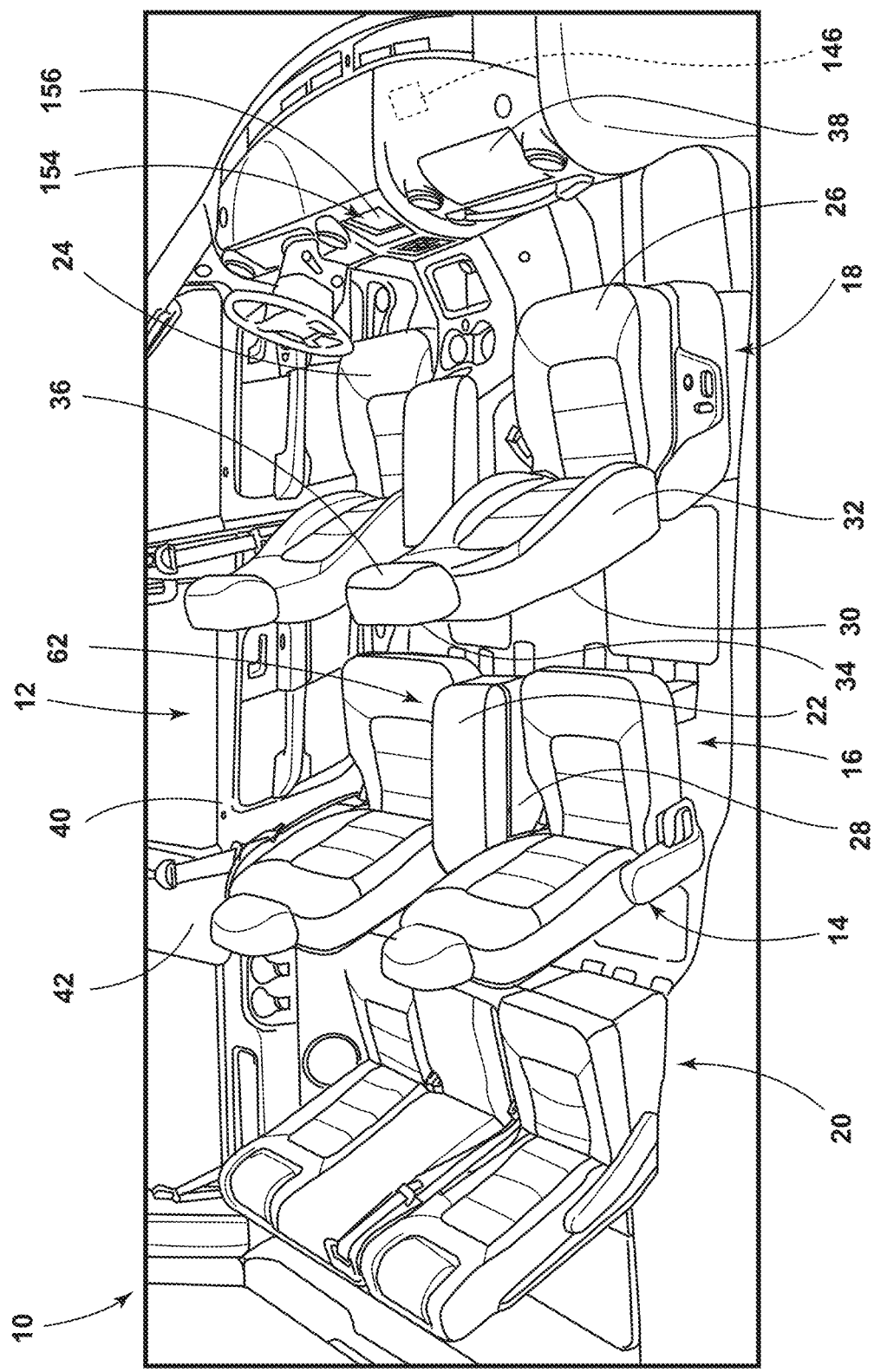
FIG. 1 is a side perspective view of an interior of a vehicle, illustrating a console disposed next to a seating assembly and a disinfecting apparatus at the console.

For purposes of description herein, the terms "rearward" and derivatives thereof, shall relate to the invention as oriented in FIG. 1. However, it is to be understood that the invention may assume various alternative orientations, except where expressly specified to the contrary. It is also to be understood that the specific devices and processes illustrated in the attached drawing, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 2:
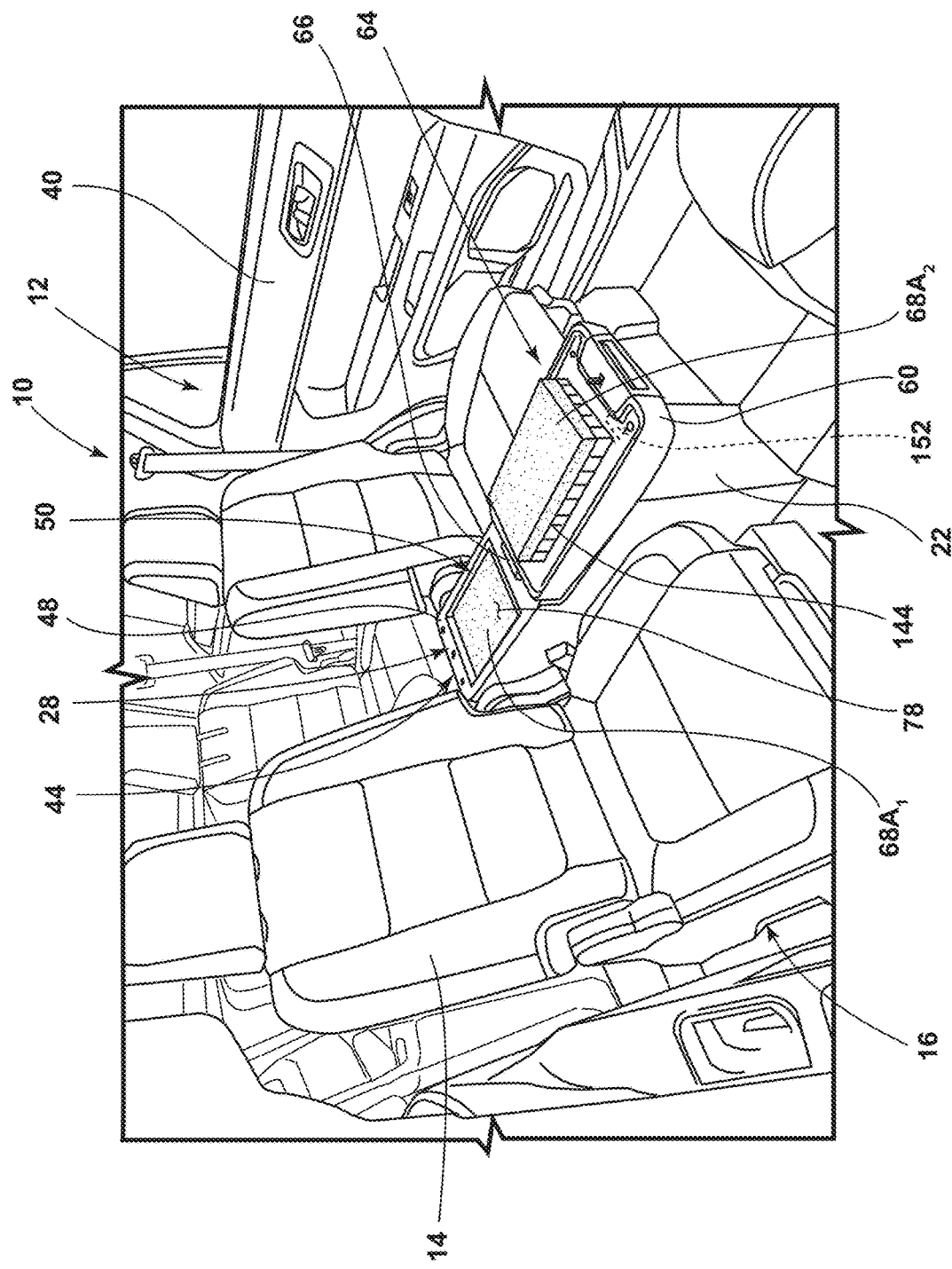
FIG. 2 is a perspective view of the interior of the vehicle of FIG. 1, illustrating a housing of the disinfecting apparatus having a lid in an open position and hingedly attached to a base, and further illustrating a light guide disposed at the base and a second light guide disposed at the lid.

Referring now to FIGS. 1 and 2, a vehicle 10 includes an interior 12. In embodiments, the vehicle 10 further includes a seating assembly 14. In the illustrated embodiment, the seating assembly 14 is part of a second row of seating 16 disposed rearward of a first row of seating 18 and forward of a third row of seating 20. In embodiments, the vehicle 10 further includes a console 22 that is disposed proximate the seating assembly 14. The location of the console 22 in the illustrated embodiments is just exemplary and the console 22 could be located anywhere in the interior 12, such as between seating assemblies 24, 26 of the first row of seating 18. The vehicle 10 further includes a disinfection apparatus 28. In embodiments, the console 22 includes the disinfection apparatus 28. However, the disinfection apparatus 28 could be disposed anywhere in connection with the vehicle 10, such as a rear side 30 of a seatback 32 of the seating assembly 26, a rear side 34 of a headrest 36 of the seating assembly 26, within a glove box 38, at a door 40, at a vertical panel 42, and so on. The vehicle 10 can be an automobile, a truck, a van, a sports utility vehicle, a bus, an airplane, a train passenger car, and the like. The vehicle 10 can be utilized for personal transportation, public transportation, as part of a ride-sharing service, as part of ride-hailing service, and so on.

Referring now additionally to FIGS. 3A-5B, the disinfection apparatus 28 includes a housing 44. As will be explained in more detail below, an occupant places an item 46 to be disinfected in the housing 44. In embodiments, the housing 44 includes a base 48 that provides an interior chamber 50. The base 48 can be part of the console 22, as in the illustrated embodiment, disposed into the rear side 30 of the seatback 32 of the seating assembly 26, or disposed at the vertical panel 42, and so on. In embodiments, the base 48 includes a primary surface 52 and at least one secondary surface 54 extending from the primary surface 52, which together form the interior chamber 50. For example, in the illustrated embodiment, side surfaces 54a-54d extending at least approximately orthogonally from the primary surface 52, with side surfaces 54a, 54c opposing each other, and side surfaces 54b, 54d opposing each other.

The disinfection apparatus 28 further includes a source 56 of ultraviolet radiation 58. The source 56 of ultraviolet radiation 58 is configured to emit ultraviolet radiation 58 into the housing 44, such as within the interior chamber 50 of the base 48. The phrase "ultraviolet radiation" means electromagnetic radiation having a wavelength within a range of 10 nm to 400 nm. In embodiments, like the illustrated embodiment, the source 56 of ultraviolet radiation 58 is one or more light emitting diodes ("LEDs"), which are disposed on the base 48 at the side surface 54c. In other embodiments, the source 56 of ultraviolet radiation 58 is a light pipe that guides ultraviolet radiation 58 from an LED disposed elsewhere in the vehicle 10 into the interior chamber 50. In embodiments, the source 56 of ultraviolet radiation 58 is an LED that emits electromagnetic radiation have a peak intensity within a wavelength range of 200 nm to 300 nm, such as within the range wavelength range of 265 nm to 275 nm. In embodiments, the source 56 of ultraviolet radiation 58 is a mercury lamp. In embodiments, the source 56 of ultraviolet radiation 58 is a UV-C LED. An example UV-C LED is model XST-35-35UV from Luminus Devices, Inc. (Sunnyvale, Calif., USA).

In embodiments, the housing 44 further includes a lid 60. The lid 60 has a closed position 62 (see, e.g., FIG. 1). In the closed position 62, the lid 60 covers the interior chamber 50 of the base 48. By covering the interior chamber 50, the lid 60 reduces or essentially eliminates leakage of ultraviolet radiation 58 from the interior chamber 50 to the exterior of the disinfection apparatus 28. In addition, the lid 60 has an open position 64 (see, e.g., FIGS. 2, 3A, 3B). In the open position 64, the lid 60 does not cover the interior chamber 50 of the base 48. By not covering the interior chamber 50, the lid 60 allows an occupant to insert the item 46 to be disinfected into the interior chamber 50 of the disinfection apparatus 28 to be disinfected with ultraviolet radiation 58. The lid 60 is manipulable to, from, and between the closed position 62 and the open position 64. In embodiments, the lid 60 is operably connected to the base 48, such as with a hinge 66. In other embodiments, the lid 60 is attached to the base 48 in the closed position 62 but is separated from the base 48 in the open position 64.

In embodiments, the housing 44 further includes a light guide $68A_1$. The light guide $68A_1$ accepts the ultraviolet radiation 58 that the source 56 of ultraviolet radiation 58 emits and guides the ultraviolet radiation 58 within the interior chamber 50. The light guide $68A_1$ has a rectangular pad-like structure (see particularly FIG. 4A), with a length 70 extending between side surfaces 72a, 72c, a width 74 orthogonal to the length 70 that extends between side surfaces 72b, 72d, and a thickness 76 orthogonal to both the length 70 and the width 74 that extends between a contact surface 78 and an opposite surface 80. The length 70 and the width 74 are substantially greater than the thickness 76. The contact surface 78 is the surface that contacts the item 46 that the occupant inserts into the disinfection apparatus 28 to be disinfected. The contact surface 78 is open to the interior chamber 50, when the lid 60 is in the open position 64. The opposite surface 80 of the light guide $68A_1$ faces in a generally opposite direction as the contact surface 78, and is disposed over the primary surface 52 of the base 48 either directly or with intermediate materials placed between the primary surface 52 of the base 48 and the opposite surface 80 of the light guide $68A_1$ (as discussed below). In such embodiments, one of the side surfaces 72a-72d of the light guide $68A_1$, such as the side surface 72c, is placed adjacent to the source 56 of ultraviolet radiation 58, such as abutting the source 56 of ultraviolet radiation 58. Side surfaces 72a-72d of the light guide $68A_1$ are disposed proximate the side surfaces 52a-52d of the base 48, respectively. A portion of the ultraviolet radiation 58 that the source 56 of ultraviolet radiation 58 emits transmits through the side surface 72c of the light guide $68A_1$. A portion of the ultraviolet radiation 58 that transmits through the side surface 72c reflects internally within the light guide $68A_1$ and then transmits through the contact surface 78. In embodiments, the light guide $68A_1$ includes projections 82 extending outward from the contact surface 78, recesses 84 extending inward into the thickness 76 of the light guide $68A_1$ from the contact surface 78, or both projections 82 and recesses 84. The internal reflection of the ultraviolet radiation 58 distributes the ultraviolet radiation 58 throughout the interior chamber 50 of the housing 44. The projections 82 and the recesses 84 disrupt the internal reflection of the ultraviolet radiation 58 within the light guide $68A_1$, and a portion of the ultraviolet radiation 58 transmits through the contact surface 78 through the projections 82 and recesses 84 to enter the interior chamber 50 of the base 48. In other words, the light guide $68A_1$ guides the ultraviolet radiation 58 from the source 56 of ultraviolet radiation 58, through the contact surface 78, and into the interior chamber 50. In embodiments, the light guide $68A_1$ lies within the interior chamber 50 of the base 48 without attaching the light guide $68A_1$ to the base 48. In embodiments, the light guide $68A_1$ is disposed within the interior chamber 50 of the base 48 and operably coupled to the base 48, such as with the side surface 72c adjacent to the source 56 of ultraviolet radiation 58 attached to the side surface 54c of the base 48 where the source 56 of ultraviolet radiation 58 is disposed. In embodiments, the light guide $68A_1$ is attached to the lid 60 and is only disposed within the interior chamber 50 when the lid 60 is in the closed position 62, which places the side surface 72c of the light guide $68A_1$ adjacent to the source 56 of ultraviolet radiation 58. In embodiments, the thickness 76 of the light guide $68A_1$ decreases as a function of the distance from the side surface 72c adjacent the source 56 of ultraviolet radiation 58. That is, the thickness 76 of the light guide $68A_1$ is greatest at the side surface 72c and the least at the side surface 72a, with the thickness 76 decreasing from the side surface 72c toward the side surface 72a. For example, the thickness 76 at the side surface 72c can be approximately 3 mm, while the thickness 76 at the side surface 72a can be approximately 1 mm.

In embodiments, the disinfection apparatus 28 further includes a second light guide $68A_2$ disposed at the other of the base 48 and the lid 60 than where the light guide $68A_1$ is disposed. For example, if the light guide $68A_1$ is disposed at the base 48, then the second light guide $68A_2$ is attached to the lid 60. In embodiments, the second light guide $68A_2$ is a mirror image of the light guide $68A_1$. The second light guide $68A_2$ (see particularly FIG. 4B) has a thickness 86 extending from a contact surface 88 to an opposite surface 90. The contact surface 88 of the second light guide $68A_2$ faces the contact surface 78 of the light guide $68A_1$ when the lid 60 is in the closed position 62. In embodiments, the opposite surface 90 is attached to the lid 60. The second light guide $68A_2$ has a length 92 extending from a side surface 98a to a side surface 98c. In the embodiment illustrated at FIG. 5B, when the lid 60 is in the open position 64, the side surface 98c is separated from and does not abut the source 56 of ultraviolet radiation 58. However, when the lid 60 is in the closed position 62, the side surface 98c is disposed adjacent to (such as abuts) the source 56 of ultraviolet radiation 58, such as source 56a. The second light guide $68A_2$ accepts the ultraviolet radiation 58 from the source 56 of ultraviolet radiation 58 through the side surface 98c. The second light guide $68A_2$ guides the ultraviolet radiation 58 via internal reflection within the interior chamber 50, when the lid 60 is in the closed position 62. The second light guide $68A_2$ has a width 96 that extends from a side surface 98b to a side surface 98d. When the lid 60 is in the closed position 62, the side surfaces 98a-98d face the side surfaces 54a-54d, respectively, of the base 48. Like the first light guide $68A_1$, the thickness 86 of the second light guide $68A_2$ decreases from the side surface 98c to the side surface 98a. For example, the thickness 86 at the side surface 98c can be approximately 3 mm, while the thickness 86 at the side surface 98a can be approximately 1 mm.

Figure 7A:
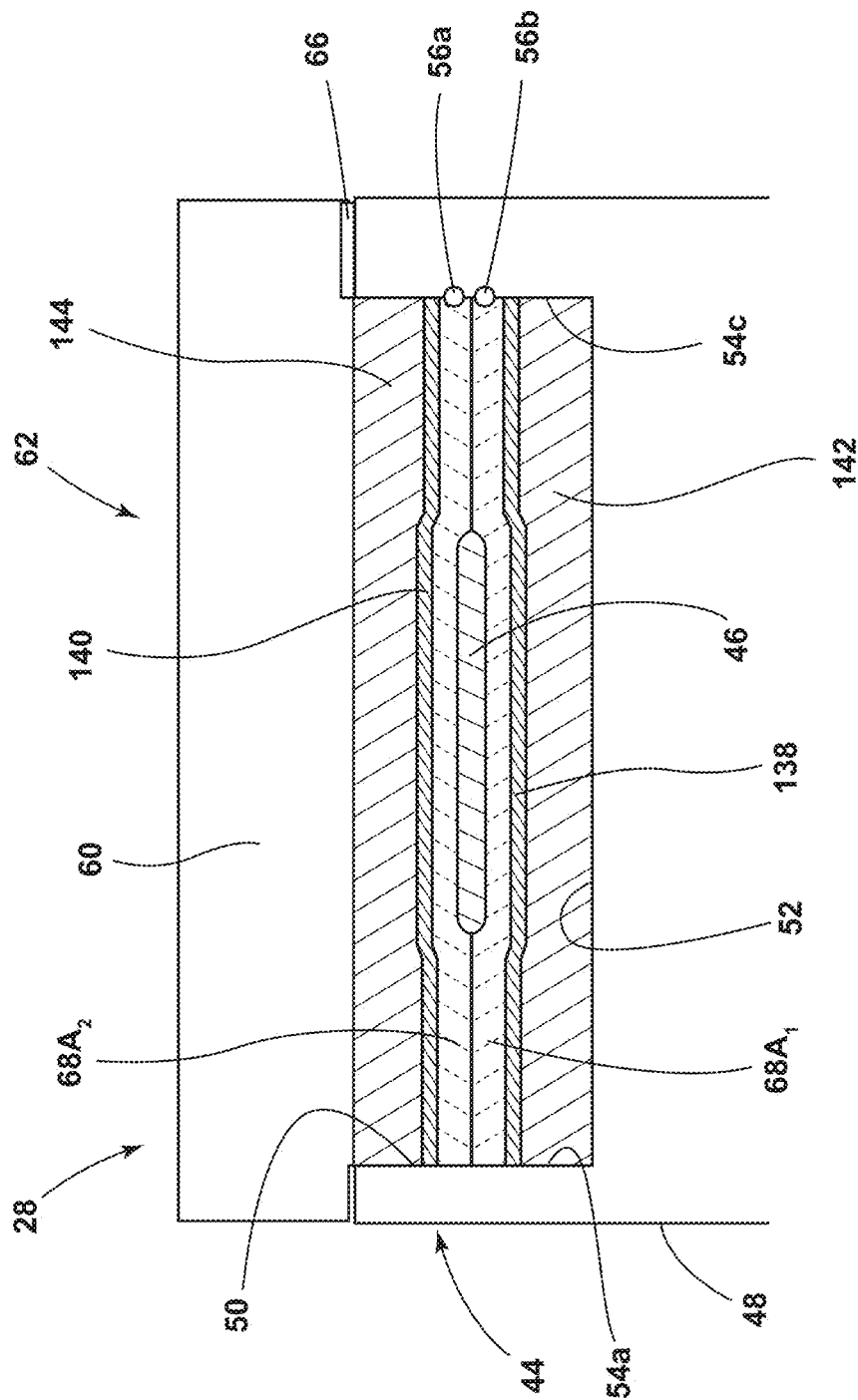
FIG. 7A is an elevational view of the cross-section taken through line VIIA-VIIA of FIG. 6, illustrating the item to be disinfected sandwiched between the light guide and the second light guide of FIGS. 2, 3A, 4A, 4B, and 5A, with the compressive layer and the second compressive layer forcing the light guide and the second light guide closer together, and further illustrating a source of ultraviolet radiation abutting the light guide and a source of ultraviolet radiation abutting the second light guide.
Figure 7B:
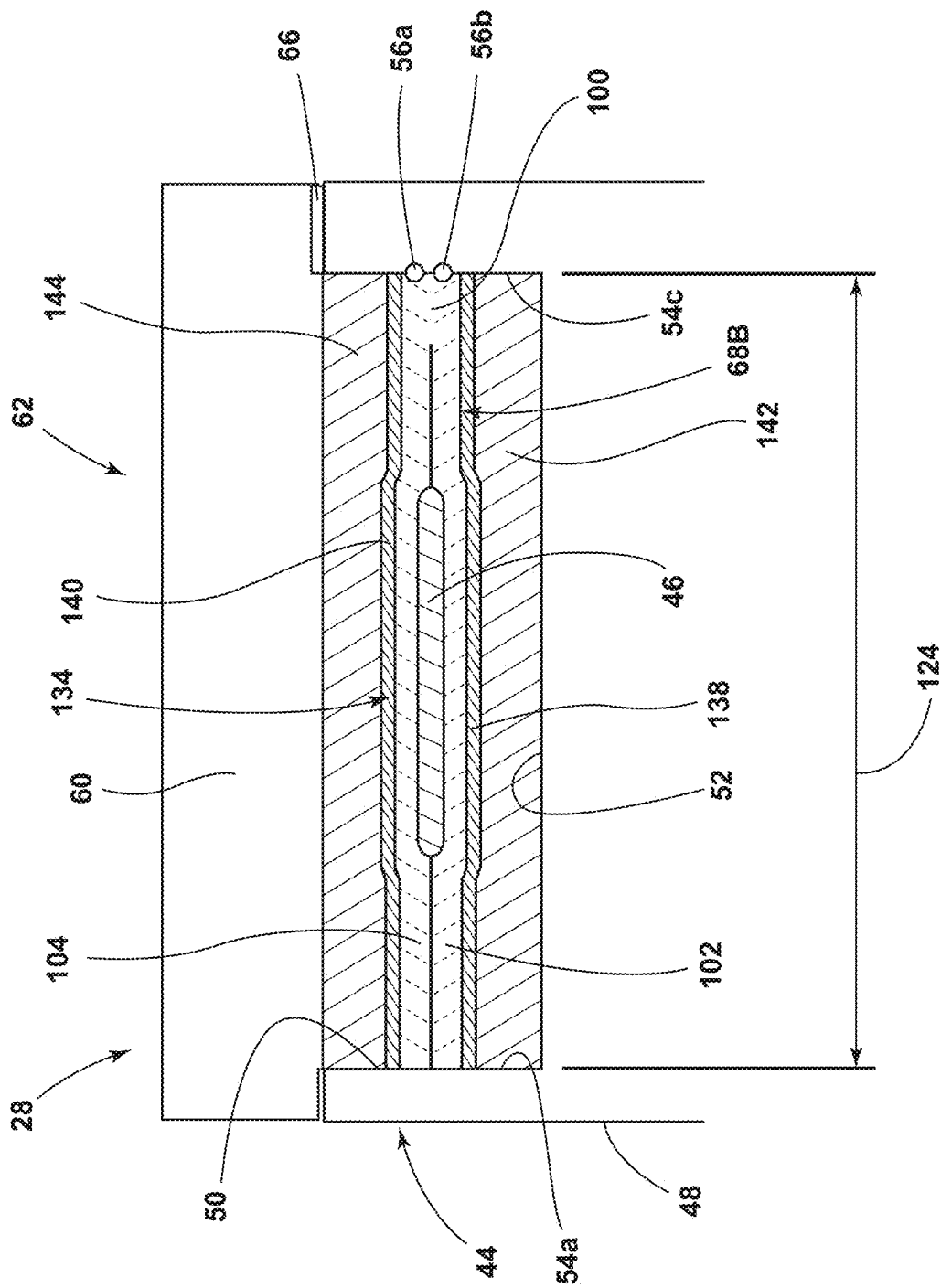
FIG. 7B is an elevational view of the cross-section taken through line VIIB-VIIB of FIG. 6, illustrating the item to be disinfected sandwiched between the first portion and the second portion of the light guide of FIGS. 3B, 4C, and 5B, with the compressive layer and the second compressive layer forcing the first portion and the second portion closer together, and further illustrating the source of ultraviolet radiation abutting the binding portion to direct ultraviolet radiation into the first portion and the second portion of the light guide.
Figure 8A:
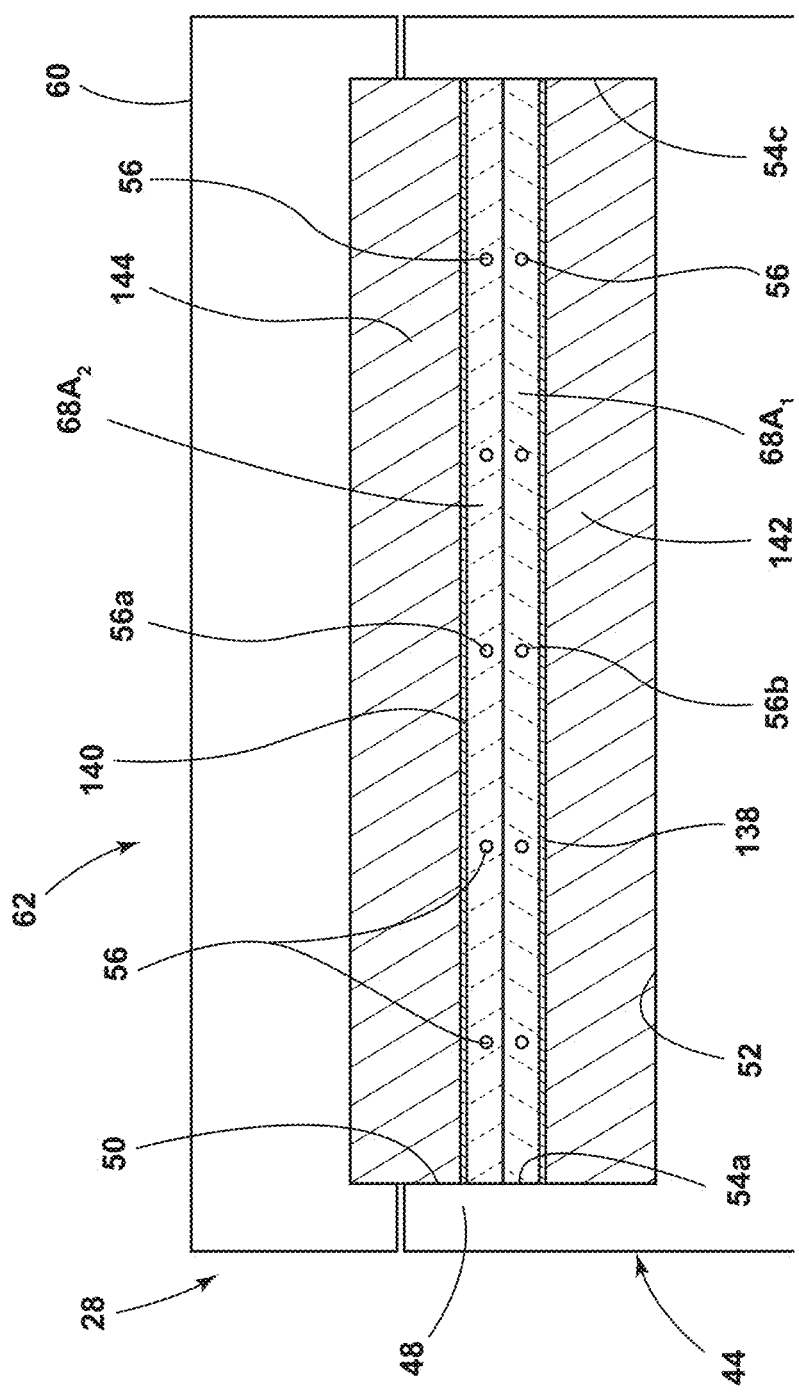
FIG. 8A is an elevational view of the cross-section taken through line VIIIA-VIIIA of FIG. 6, illustrating the first light guide and the second light guide of FIGS. 2, 3A, 4A, 4B, 5A, and 7A each abutting sources of ultraviolet radiation, and further illustrating the reflective layer and the second reflective layer positioned to reflect emitted ultraviolet radiation back in the first light guide and the second light guide rather than be absorbed by the housing, the compressive layer, or the second compressive layer.
Figure 8B:
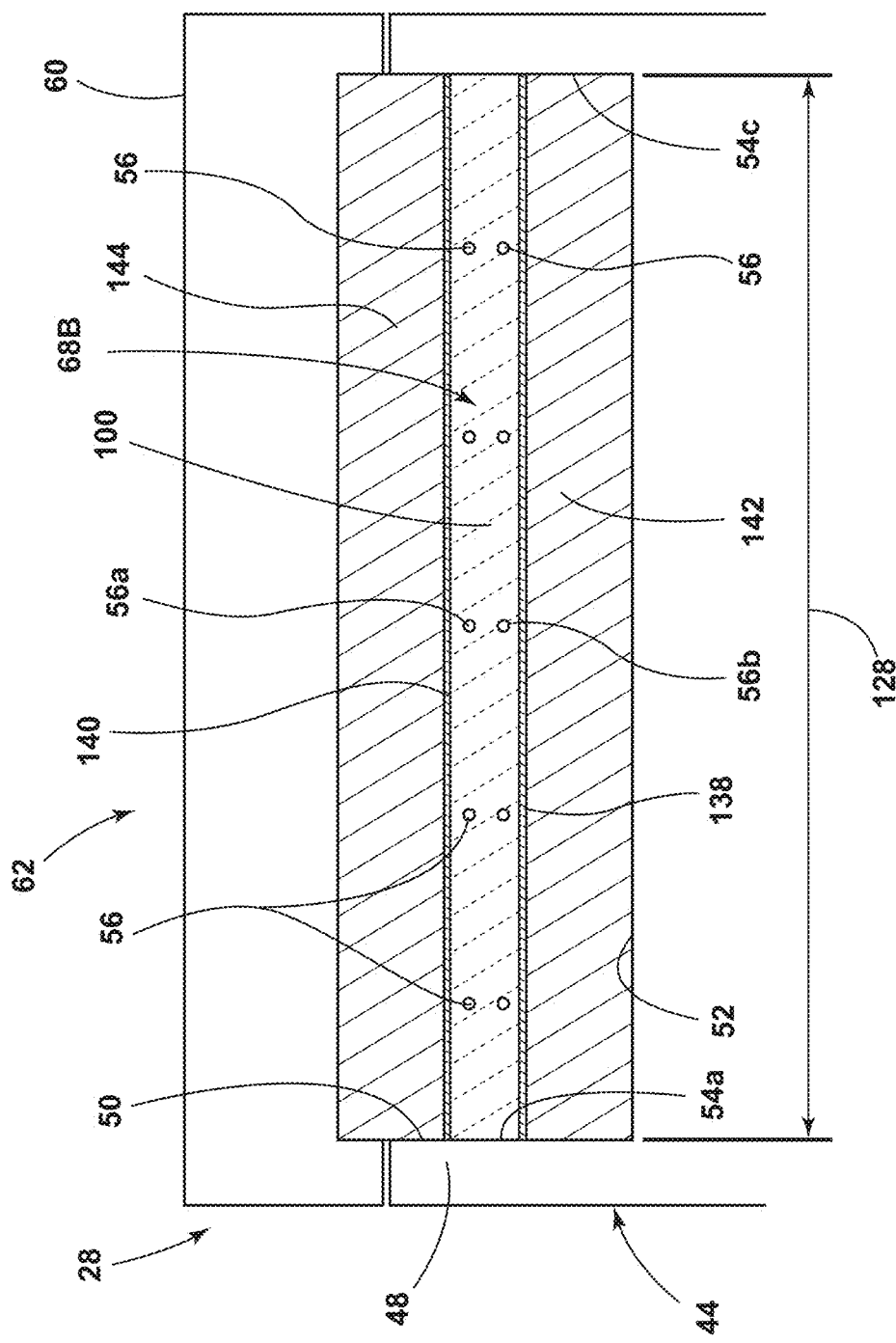
FIG. 8B is an elevational view of the cross-section taken through line VIIIB-VIIIB of FIG. 6, illustrating the light guide of FIGS. 3B, 4C, 5B, and 7B abutting sources of ultraviolet radiation, and further illustrating the reflective layer and the second reflective layer positioned to reflected emitted ultraviolet radiation back into the light guide.

In other embodiments, a light guide 68B is a essentially a combination of the light guide $68A_1$ and the second light guide $68A_2$ being connected at a binding portion 100 to form a book-like structure with the light guide $68A_1$ becoming a first portion 102 of the light guide 68B and the second light guide $68A_2$ becoming a second portion 104 of the light guide 68B. The first portion 102 is therefore substantially like the embodiment of the light guide $68A_1$ described in connection with FIG. 4A, having a thickness 106 (see particularly FIG. 4C) extending from a contact surface 108 to an opposite surface 110, a length 112 extending from a side surface 114a to a side surface 114c at the binding portion 100, and a width 116 extending from a side surface 114b to a side surface 114d. The second portion 104 is also substantially like the embodiment of the second light guide $68A_2$ described in connection with FIG. 4B, having a thickness 118 from a contact surface 120 to an opposite surface 122, a length 124 (see FIG. 7B) from a side surface 126a to the side surface 114c (shared with the first portion 102 at the binding portion 100), and a width 128 (see FIG. 8B) from a side surface 126b to a side surface 126d. The surface side 114c at the binding portion 100 thus extends between the opposite surface 80 of the first portion 102 and the opposite surface 122 of the second portion 104. The second portion 104 has an open position 132 relative to the first portion 102 in which the contact surface 120 of the second portion 104 is separated from the contact surface 108 of the first portion 102. In addition, the second portion 104 has a closed position 134 (see, e.g., FIG. 7B) relative to the first portion 102 in which the contact surface 120 of the second portion 104 is disposed adjacent (such as contacting) the contact surface 108 of the first portion 102. The contact surface 78 of the first portion 102 is open to the interior chamber 50, when the lid 60 is in the open position 64 and the second portion 104 is in the open position 132. The contact surface 108 of the first portion 102 and the contact surface 120 of the second portion 104 are brought closer together as the second portion 104 is manipulated from the open position 132 to the closed position 134. In use, as described below, the occupant places the item 46 to be disinfected between the contact surfaces 108, 120 of the first portion 102 and the second portion 104, respectively. The opposite surface 110 of the first portion 102 faces in a generally opposite direction as the contact surface 108, and is disposed over the primary surface 52 of the base 48 either directly or with intermediate materials placed between the primary surface 52 of the base 48 and the opposite surface 80 of the first portion 102 (as discussed below). The opposite surface 122 of the second portion 104 of the light guide 68B faces in a generally opposite direction as the contact surface 120 of the second portion 104, and is disposed adjacent the lid 60 when both the second portion 104 and the lid 60 are in their respective closed positions 62, 134. The side surfaces 114a, 114b, 114d of the first portion 102 face toward the side surfaces 54a, 54b, 54d, respectively, of the base 48. When the second portion 104 is in the closed position 134, the side surfaces 126a, 126b, 126d of the second portion 104 face toward the side surfaces 54a, 54b, 54d, respectively, of the base 48. The side surface 114c at the binding portion 100 is disposed adjacent to (such as abutting) the source 56 of ultraviolet radiation 58 and the side surface 54c of the base 48. For example, a source 56b of ultraviolet radiation 58 is positioned to emit ultraviolet radiation 58 into the first portion 102 through the side surface 114c, while the source 56a of ultraviolet radiation 58 is positioned to emit ultraviolet radiation 58 into the second portion 104 through the side surface 114c. In embodiments, the contact surface 108 of the first portion 102 and the contact surface 120 of the second portion 104 include the projections 82 or the recesses 84, or both the projections 82 and the recesses 84. A portion of the ultraviolet radiation 58 that the source 56 of ultraviolet radiation 58 emits transmits through the side surface 114c of the binding portion 100 of the light guide 68B, into the first portion 102 and into the second portion 104 of the light guide 68B. The ultraviolet radiation 58 transmitted through the side surface 114c transmits throughout the first portion 102 and the second portion 104 via internal reflection. A portion of the ultraviolet radiation 58 internally reflected transmits out of the light guide 68B through the contact surfaces 108, 120 of the first portion 102 and the second portion 104. In embodiments, the light guide 68B lies within the interior chamber 50 of the base 48 without attaching the light guide 68B to the base 48. In embodiments, the light guide 68B is disposed within the interior chamber 50 of the base 48 and is operably coupled to the base 48, such as with the side surface 114c at the binding portion 100 attached to the side surface 54c of the base 48 at which the source 56 of ultraviolet radiation 58 is disposed. In embodiments, the second portion 104 of the light guide 68B is attached to the lid 60, such that when the lid 60 is manipulated to the open position 64, the second portion 104 of the light guide 68B is forced to the open position 132. In embodiments, the thicknesses 106, 118 of both the first portion 102 and the second portion 104, respectively, decrease from the binding portion 100 toward the side surfaces 114a, 126a. For example, the combined thicknesses 106, 118 of the first portion 102 and the second portion 104 at the side surface 114c of the binding portion 100 can be 6 mm, and the thicknesses 106, 118 at or near the side surfaces 114a, 126a of the first portion 102 and the second portion 104, respectively, can each be 1 mm. In embodiments, the first portion 102 of the light guide 68B includes a flap 136 contiguous with side surfaces 114a, 114b, 114d of the first portion 102 that extends orthogonally from the contact surface 108 away from the primary surface 52 of the base 48. When the second portion 104 is in the closed position 134, the flap 136 faces the side surfaces 126a, 126b, 126d of the second portion 104. When the light guide 68B includes the flap 136, the width 128 and the length 124 of the second portion 104 can be slightly smaller than the width 116 and the length 112 of the first portion 102.

In embodiments, the light guide $68A_1$, the second light guide $68A_2$, and the light guide 68B are made of a flexible material, such as silicone. In embodiments, the light guide $68A_1$, the second light guide $68A_2$, and the light guide 68B are molded from silicone. Molded silicone transmits ultraviolet radiation 58 well, in some instances having over 90 percent transmission at selected ultraviolet wavelengths. Molded silicone resists scratches. The projections 82 and recesses 84 can be formed via the molding of the silicone. An example moldable silicone for the light guide $68A_1$, the second light guide $68A_2$, and the light guide 68B is DOWSIL MS-1003 moldable silicon available from Dow (Midland, Mich., USA).

Referring now additionally to FIGS. 6-8B, in embodiments, the disinfection apparatus 28 further includes a reflective layer 138. The reflective layer 138 is disposed adjacent to (such as abuts) the opposite surface 80 of the light guide $68A_1$ (see, e.g., FIG. 7A) or the opposite surface 110 of the first portion 102 of the light guide 68B (see, e.g., FIG. 7B). In the case of the light guide $68A_1$, the reflective layer 138 reflects a portion of the ultraviolet radiation 58 that transmits through the opposite surface 80 of the light guide $68A_1$ back through the opposite surface 80 and into the light guide $68A_1$. In the case of the light guide 68B, the reflective layer 138 reflects a portion of the ultraviolet radiation 58 that transmits through the opposite surface 110 of the first portion 102 of the light guide 68B back through the opposite surface 110 and into the light guide 68B.

In embodiments, the light guide $68A_1$ is visually transparent. The light guide $68A_1$ is sufficiently visually transparent that an occupant can see through the light guide $68A_1$ through the contact surface 78, through the thickness 76 of the light guide $68A_1$, and through the opposite surface 80. In embodiments, the light guide 68B is visually transparent. The first portion 102 of the light guide 68B is sufficiently visually transparent that an occupant can see through the first portion 102 and the second portion 104 of the light guide 68B. If the disinfection apparatus 28 incorporates the reflective layer 138, then the light guide $68A_1$ or the first portion 102 of the light guide 68B is sufficiently visually transparent that an occupant can see through the light guide $68A_1$ or the first portion 102 of the light guide 68B to the reflective layer 138. In embodiments, the second light guide $68A_2$, and the second portion 104 of the light guide 68B, are visually transparent, as well. As mentioned, the surface 72c of the light guide $68A_1$ adjacent to the source 56 of ultraviolet radiation 58 is attached to the side surface 54c of the base 48 where the source 56 of ultraviolet radiation 58 is disposed. However, the opposite surface 80 of the light guide $68A_1$ is not attached or adhered to the reflective layer 138 and thus, portions of the opposite surface 80 of the light guide $68A_1$, such as near the surface 72a, is separable from the base 48. In other words, portions of the opposite surface 80 of the light guide $68A_1$ can be lifted away from the reflective layer 138. This non-adherence of the opposite surface 80 of the light guide $68A_1$ to the reflective layer 138 allows for the placement of maps, toll booth and parking lot tickets, family pictures, etc., between the light guide $68A_1$ and the reflective layer 138. Because the light guide $68A_1$ can be visually transparent, those items can be viewed through the light guide $68A_1$ without removing the items. However, in other embodiments, the opposite surface 80 of the light guide $68A_1$ is adhered to the reflective layer 138.

Similarly, for the light guide 68B, the side surface 114c of the light guide 68B at the binding portion 100 adjacent to the source 56 of ultraviolet radiation 58 is attached to the side surface 54c of the base 48 where the source 56 of ultraviolet radiation 58 is disposed. However, the opposite surface 110 of the first portion 102 of the light guide 68B is not attached or adhered to the reflective layer 138 and thus, portions of the opposite surface 110 of the first portion 102, such as near the side surface 114a, is separable from the base 48. In other words, portions of the opposite surface 110 can be lifted away from the reflective layer 138. This non-adherence of the opposite surface 110 of the first portion 102 to the reflective layer 138 allows for the placement of maps, toll booth and parking lot tickets, family pictures, etc., between the first portion 102 and the reflective layer 138. Because the first portion 102 and the second portion 104 are visually transparent, those items can be viewed through the light guide 68B without removing the items, even when the second portion 104 is in the closed position 134 and the lid 60 is in the open position 64. However, in other embodiments, the opposite surface 110 of the first portion 102 of the light guide 68B is adhered to the reflective layer 138.

In embodiments, the disinfection apparatus 28 further includes a second reflective layer 140. The second reflective layer 140 is disposed adjacent to (such as abuts) the opposite surface 90 of the second light guide $68A_2$, if the first light guide $68A_1$ and second light guide $68A_2$ are utilized. The second light guide $68A_2$ can be affixed to the second reflective layer 140. If instead the light guide 68B with the first portion 102 and the second portion 104 is utilized, then the second reflective layer 140 is disposed adjacent to (such as abuts) the opposite surface 122 of the second portion 104 of the light guide 68B, when the light guide 68B is in the closed position 134 and the lid 60 is in the closed position 62. The second reflective layer 140 reflects ultraviolet radiation 58 that transmits through the opposite surface 90 of the second light guide $68A_2$ or the opposite surface 122 of the second portion 104 of the light guide 68B back into the second light guide $68A_2$ or the second portion 104 of the light guide 68B as the case may be.

The reflective layer 138 and the second reflective layer 140, if utilized, reflects ultraviolet radiation 58 back into the light guide $68A_1$, the second light guide $68A_2$, and the light guide 68B, as the case may be, to increase the amount of ultraviolet radiation 58 emitted through the contact surfaces 78, 88, 108, 120, and onto the item 46. In embodiments of the disinfection apparatus 28 without the light guide $68A_1$, the reflective layer 138 is disposed at either the base 48 or the lid 60, or both the base 48 and the lid 60, such as at the primary surface 52 and the side surfaces 54a-54d of the base 48, and the second reflective layer 140 is disposed at the other of the base 48 or the lid 60. The reflective layer 138 and the second reflective layer 140 increase the amount of ultraviolet radiation 58 emitted from the source 56 of ultraviolet radiation 58 that irradiates upon the item 46 placed in the interior chamber 50 and decreases the amount of ultraviolet radiation 58 absorbed by the disinfection apparatus 28, such as the housing 44. In embodiments, the reflective layer 138 and the second reflective layer 140 reflect at least 40 percent, at least 45 percent, at least 50 percent, or at least 60 percent of incident electromagnetic radiation having a wavelength in a range of 200 nm to 300 nm, at a normal (90 degree) angle of incidence. In embodiments, the reflective layer 138 and the second reflective layer 140 comprise a metal, such as a metal foil. In embodiments, the reflective layer 138 and the second reflective layer 140 comprise aluminum. In embodiments, the reflective layer 138 and the second reflective layer 140 comprise biaxially-oriented polyethylene terephthalate polyester film (e.g., Mylar).

In embodiments, the disinfection apparatus 28 further includes a compressive layer 142. The compressive layer 142 is disposed between the base 48 of the housing 44 and the opposite surface 80 of the light guide $68A_1$, or the opposite surface 110 of the first portion 102 of the light guide 68B. For example, with the light guide $68A_1$, the compressive layer 142 is disposed over the primary surface 52 of the base 48, the reflective layer 138 is disposed over the compressive layer 142, and the opposite surface 80 of the light guide $68A_1$ is disposed over the reflective layer 138. As another example, with the light guide 68B, the compressive layer 142 is disposed over the primary surface 52 of the base 48, the reflective layer 138 is disposed over the compressive layer 142, and the opposite surface 110 of the first portion 102 of the light guide 68B is disposed over the reflective layer 138. In embodiments, the compressive layer 142 is attached (such as adhered) to the primary surface 52 of the base 48. In embodiments, the compressive layer 142 extends between and abuts the side surfaces 54a-54d of the base 48. When the lid 60 is in the closed position 62, the compressive layer 142 compresses the contact surface 78 of the light guide $68A_1$ against the contact surface 88 of the second light guide $68A_2$, or the contact surface 108 of the first portion 102 of the light guide 68B against the contact surface 120 of the second portion 104 of the light guide 68B.

In embodiments, the disinfection apparatus 28 further includes a second compressive layer 144. The second compressive layer 144 is disposed between the lid 60 of the housing 44 and the opposite surface 90 of the second light guide $68A_2$, or the opposite surface 122 of the second portion 104 of the light guide 68B. For example, with the second light guide $68A_2$, the second compressive layer 144 is disposed between the lid 60 and the second reflective layer 140, and the second reflective layer 140 is disposed between the opposite surface 90 of the second light guide $68A_2$ and the second reflective layer 140. As another example, with the light guide 68B, the second compressive layer 144 is disposed between the lid 60 and the second reflective layer 140, and the second reflective layer 140 is disposed between the opposite surface 122 of the second portion 104 of the light guide 68B and the second reflective layer 140. In embodiments, the second compressive layer 144 is attached (such as adhered) to the lid 60. In embodiments, when the lid 60 is in the closed position 62, the second compressive layer 144 extends between and abuts the side surfaces 54a-54d of the base 48. When the lid 60 is in the closed position 62, the compressive layer 142 and the second compressive layer 144 compress the contact surface 78 of the light guide $68A_1$ against the contact surface 88 of the second light guide $68A_2$, or the contact surface 108 of the first portion 102 of the light guide 68B against the contact surface 120 of the second portion 104 of the light guide 68B.

Figure 3A:
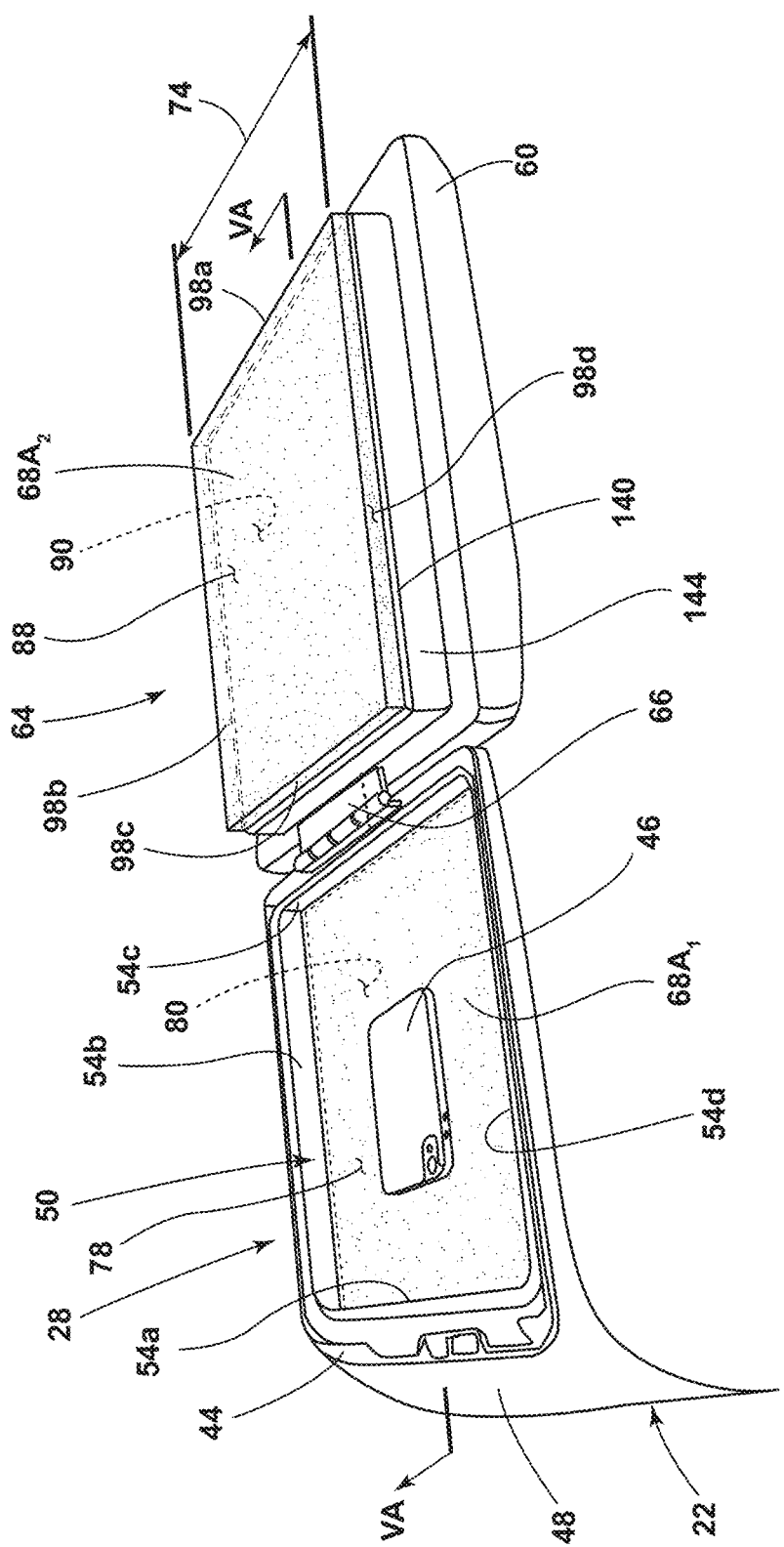
FIG. 3A is a perspective view of the disinfection apparatus of FIG. 1, illustrating an item to be disinfected placed on a contact surface of the light guide.
Figure 3B:
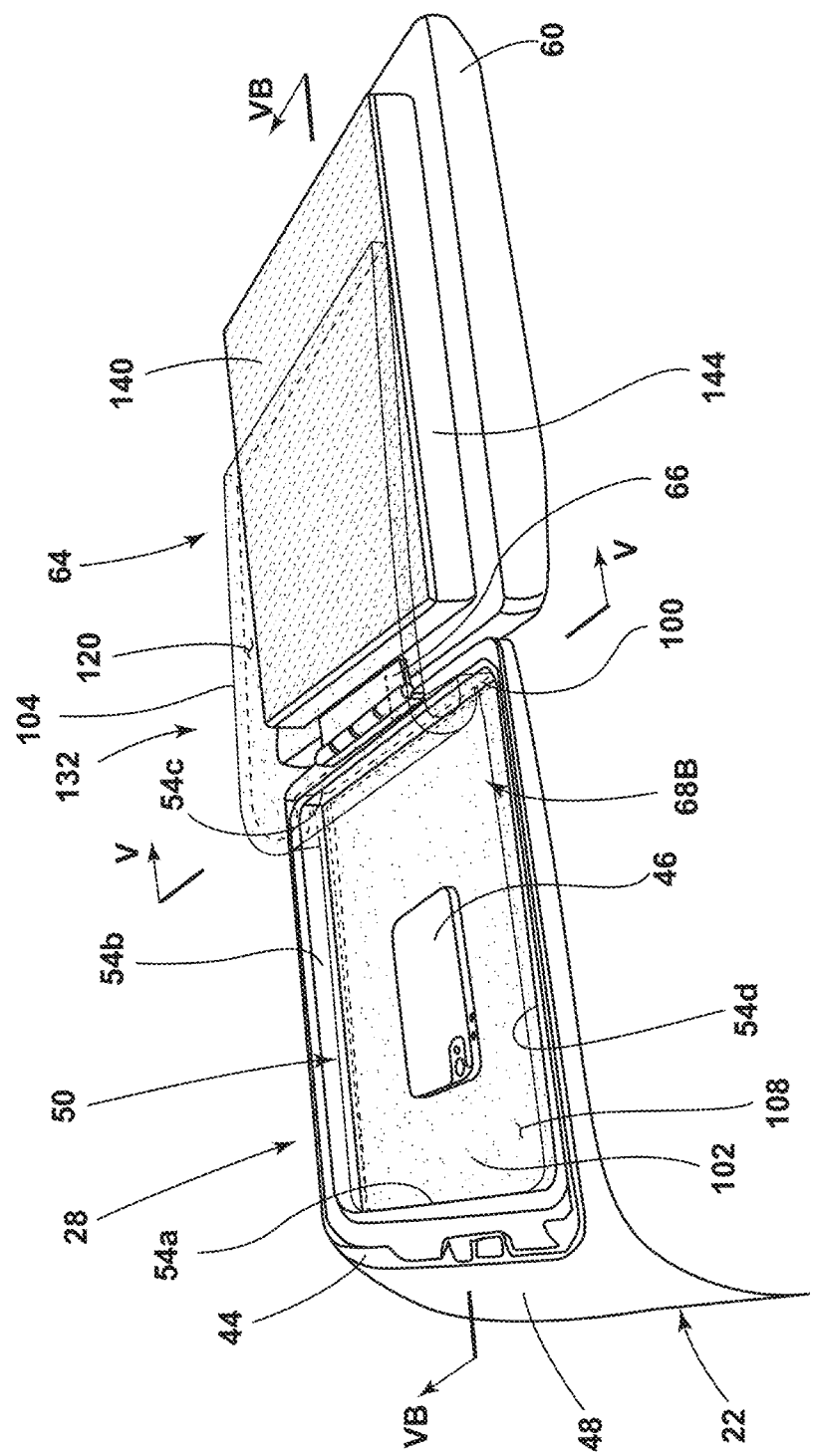
FIG. 3B is a perspective view of the disinfection apparatus of FIG. 1, but illustrating another embodiment of a light guide that has a first portion and a second portion bound together at a binding portion, and further illustrating the item to be disinfected placed on a contact surface of the first portion of the light guide.
Figure 4A:
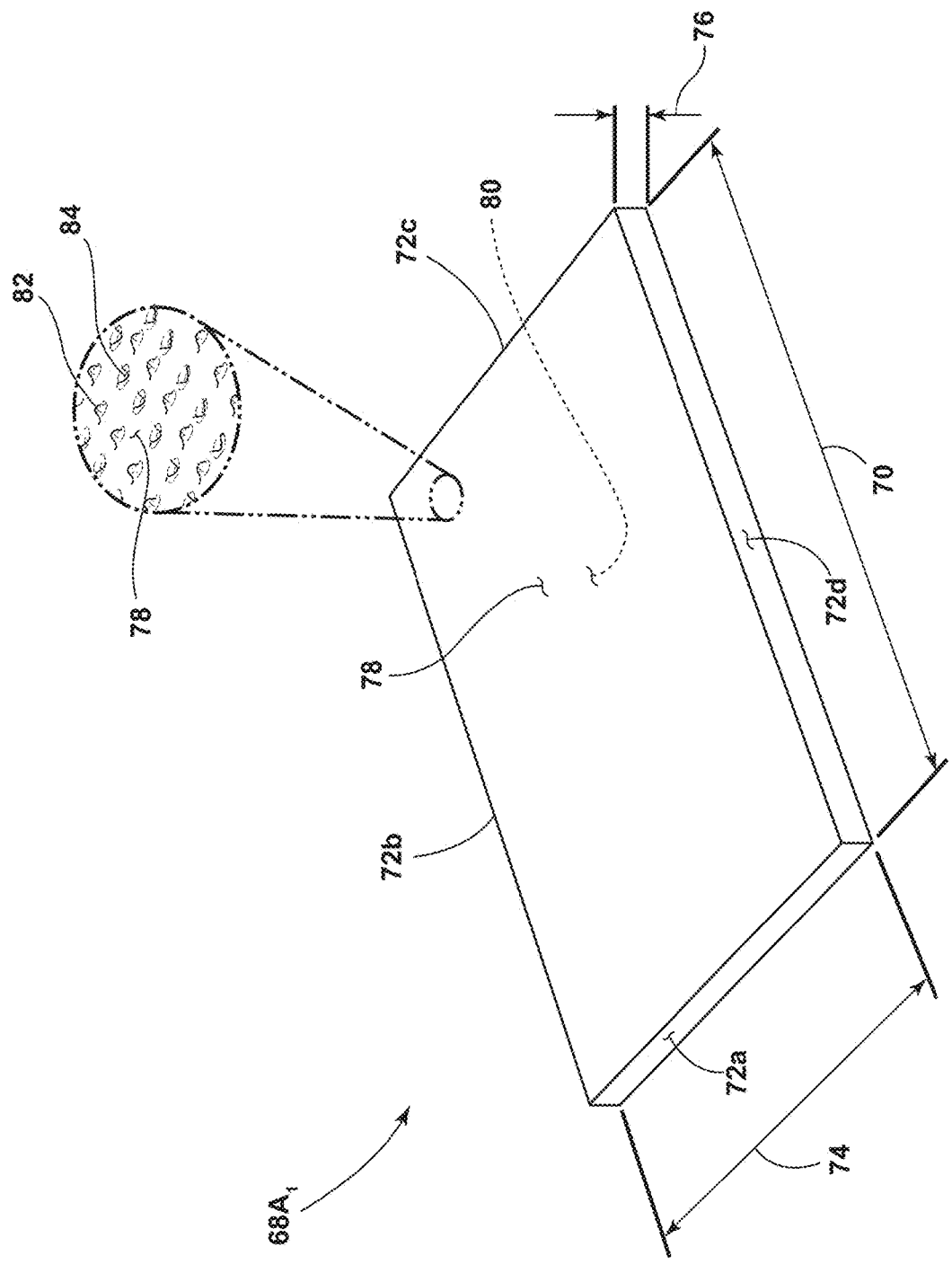
FIG. 4A is a perspective view of the light guide of FIG. 2, illustrating the light guide resembling a pad and having a thickness between the contact surface and an opposite surface, a length, and a width, with the thickness being substantially smaller than the length and the width.
Figure 4B:
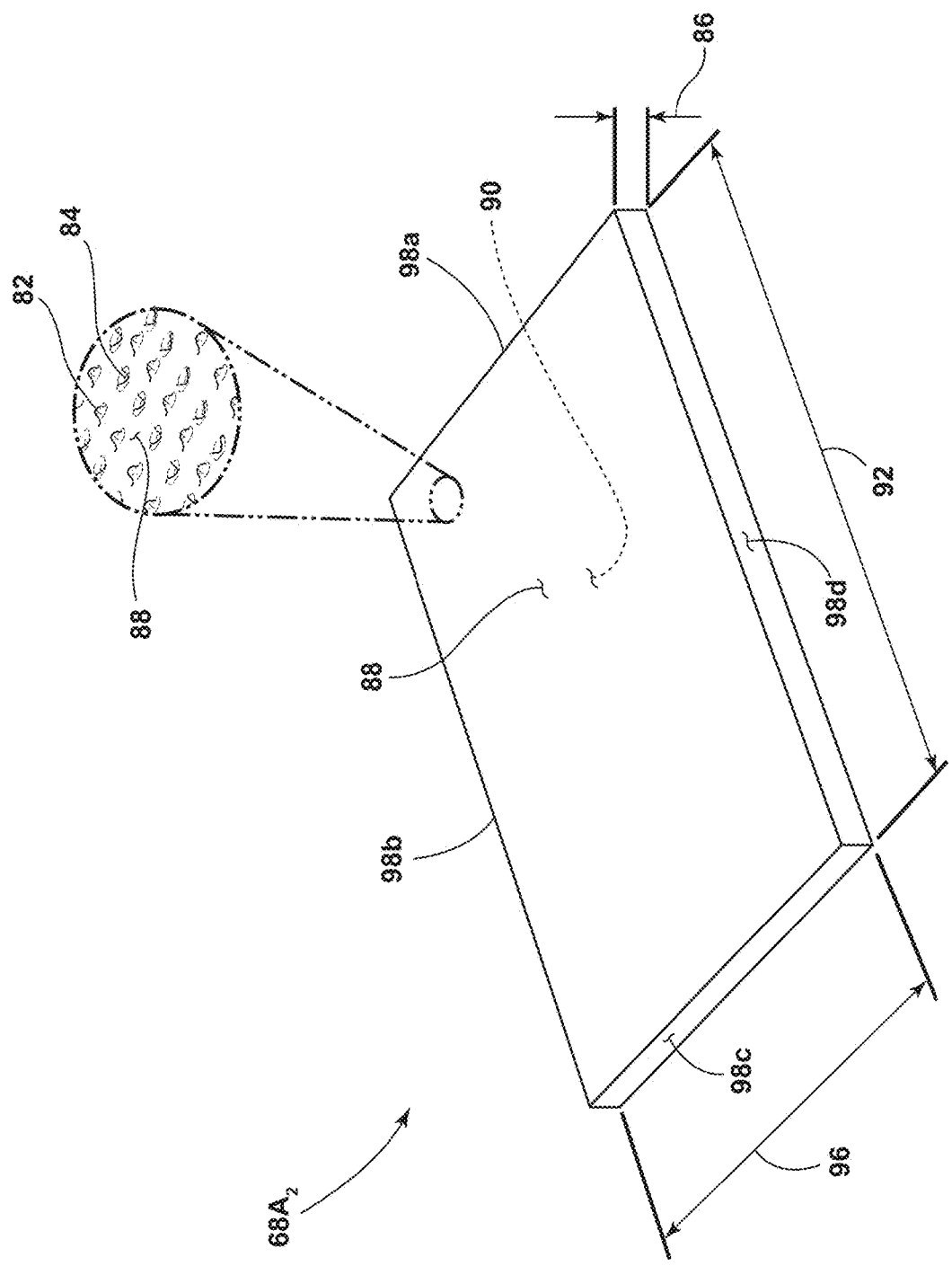
FIG. 4B is a perspective view of the second light guide of FIG. 2, illustrating the second light guide also resembling a pad and having a thickness between the contact surface and an opposite surface, a length, and a width, with the thickness being substantially smaller than the length and the width.
Figure 4C:
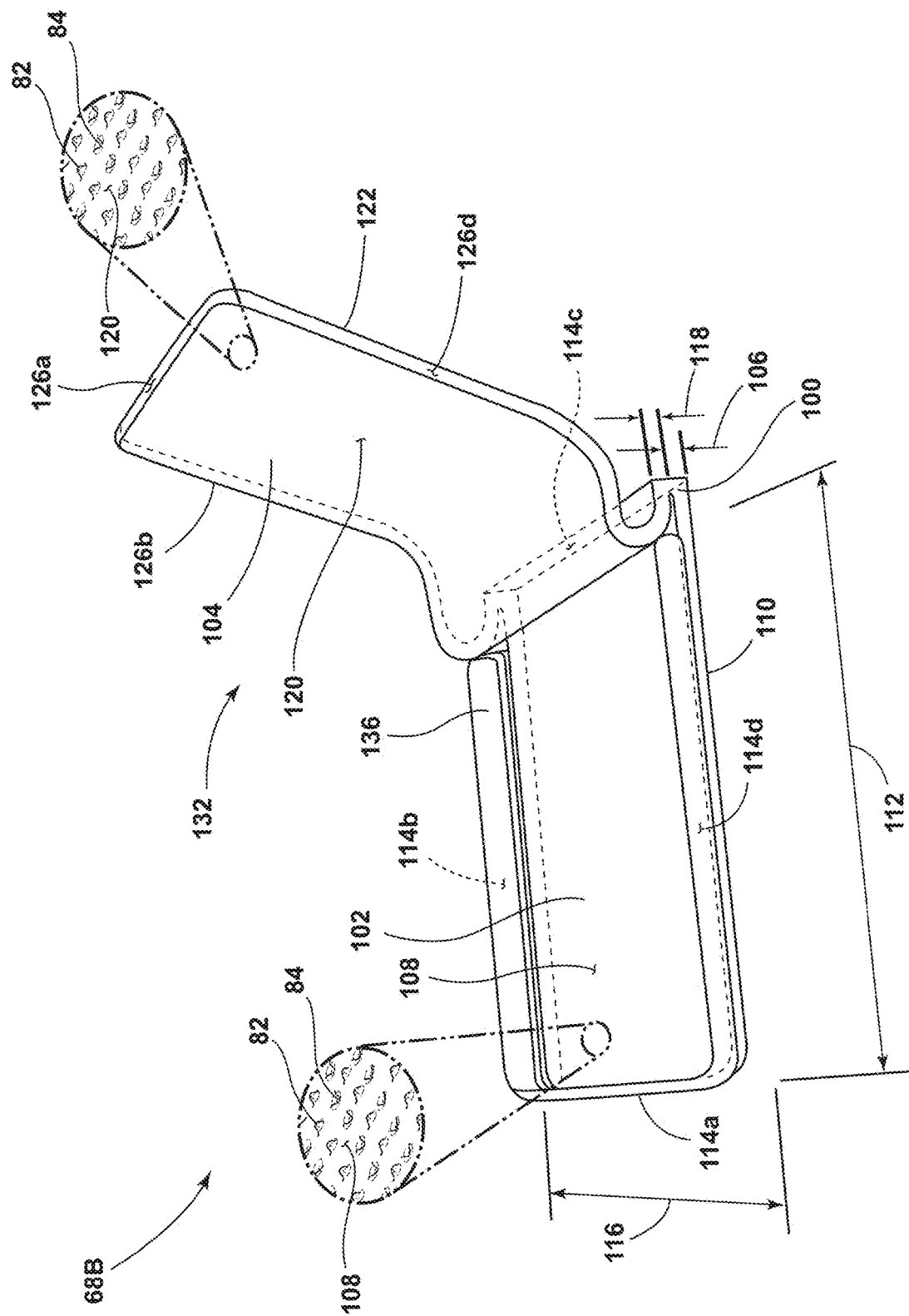
FIG. 4C is a perspective view of the light guide of FIG. 3B, illustrating the second portion in an opened position separated from the first portion.
Figure 5A:
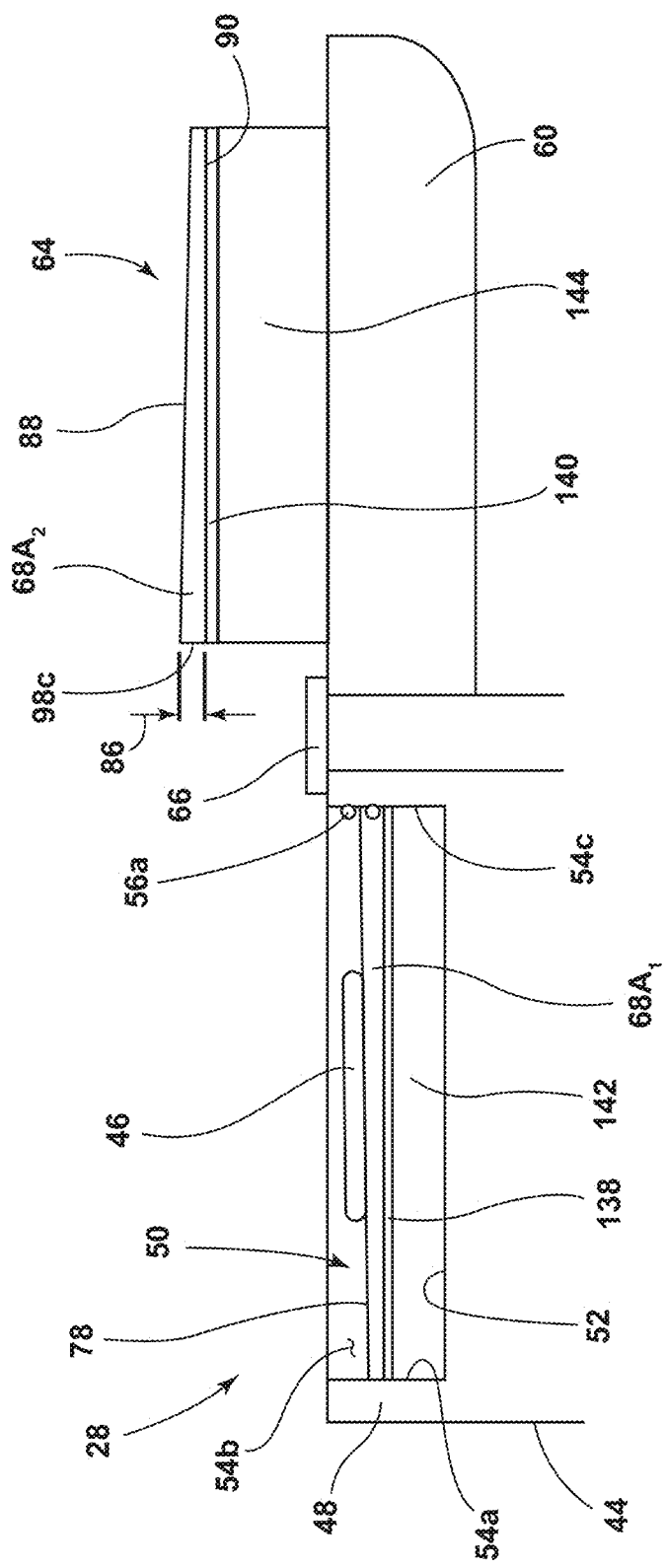
FIG. 5A is an elevational view of the cross-section taken through line VA-VA of FIG. 3A, illustrating a compressive layer disposed under a reflective layer disposed under the light guide, the item on the contact surface of the light guide, a second reflective layer between the opposite side of the second light guide and the lid, and a second compressive layer disposed between the second reflective layer and the lid.
Figure 5B:
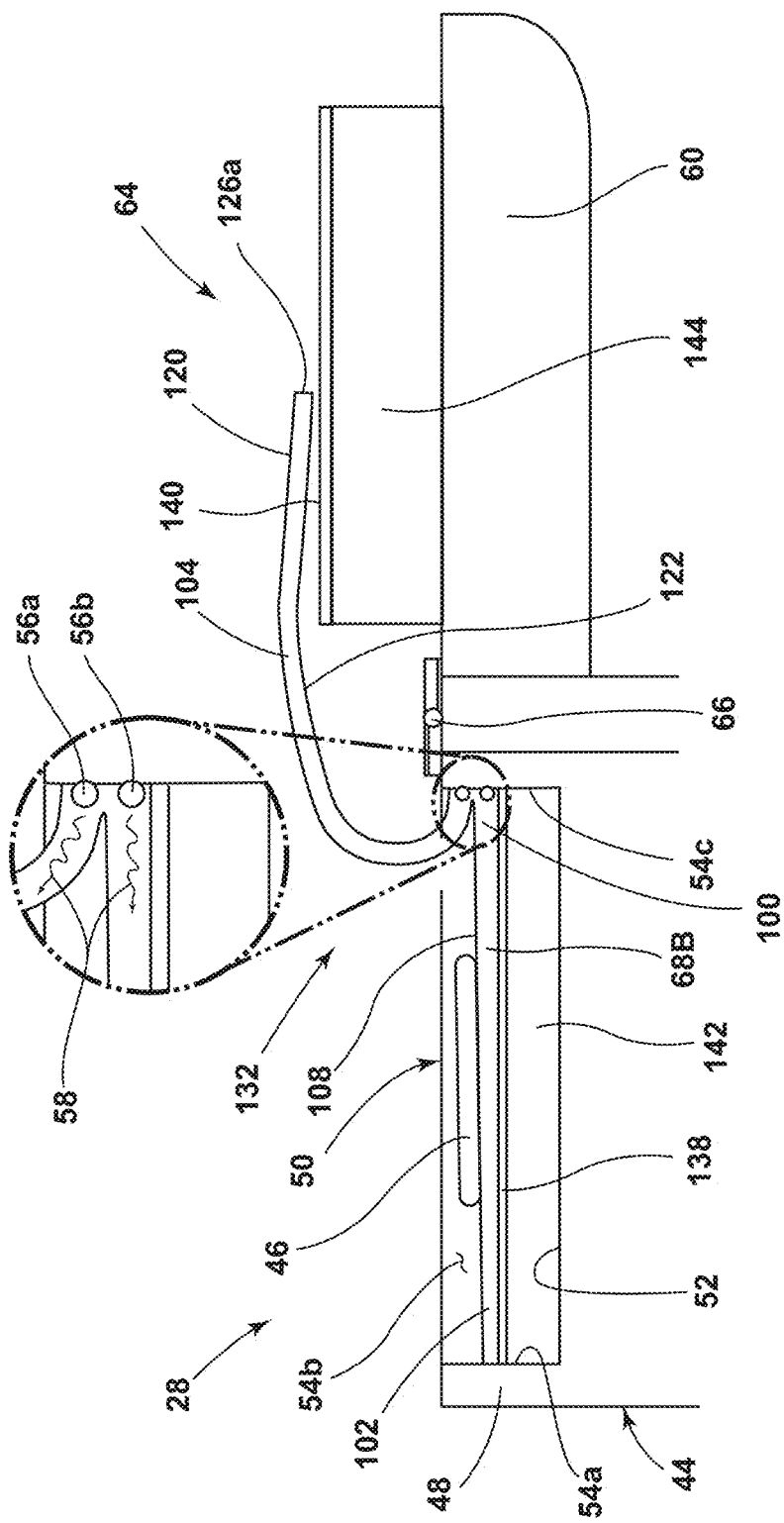
FIG. 5B is an elevational view of the cross-section taken through line VB-VB of FIG. 3B, illustrating a compressive layer disposed under the first portion of the light guide, a reflective layer disposed between the compressive layer and the first portion, a second reflective layer disposed at the lid, and a second compressive layer disposed between the lid and the second reflective layer.
Figure 6:
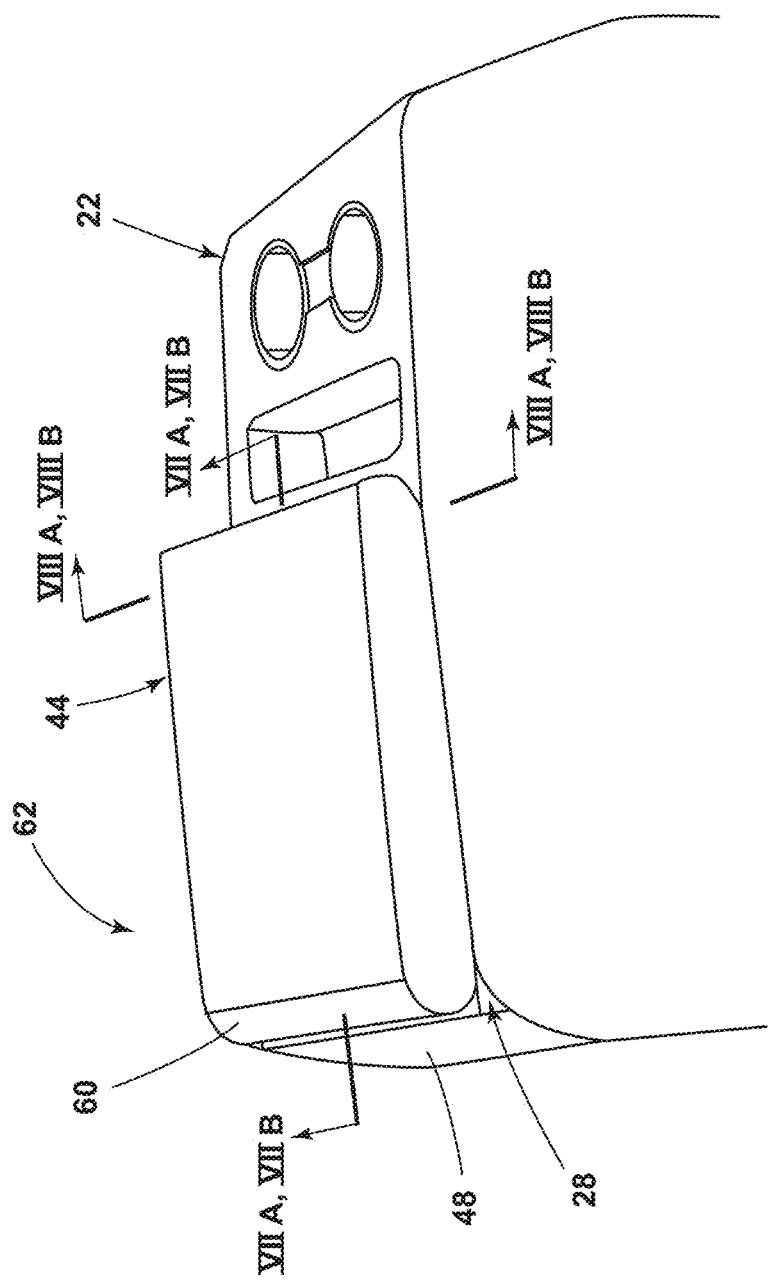
FIG. 6 is a perspective view of the disinfecting apparatus of FIG. 2, illustrating the lid of the housing in a closed position over the base.
Figure 9:
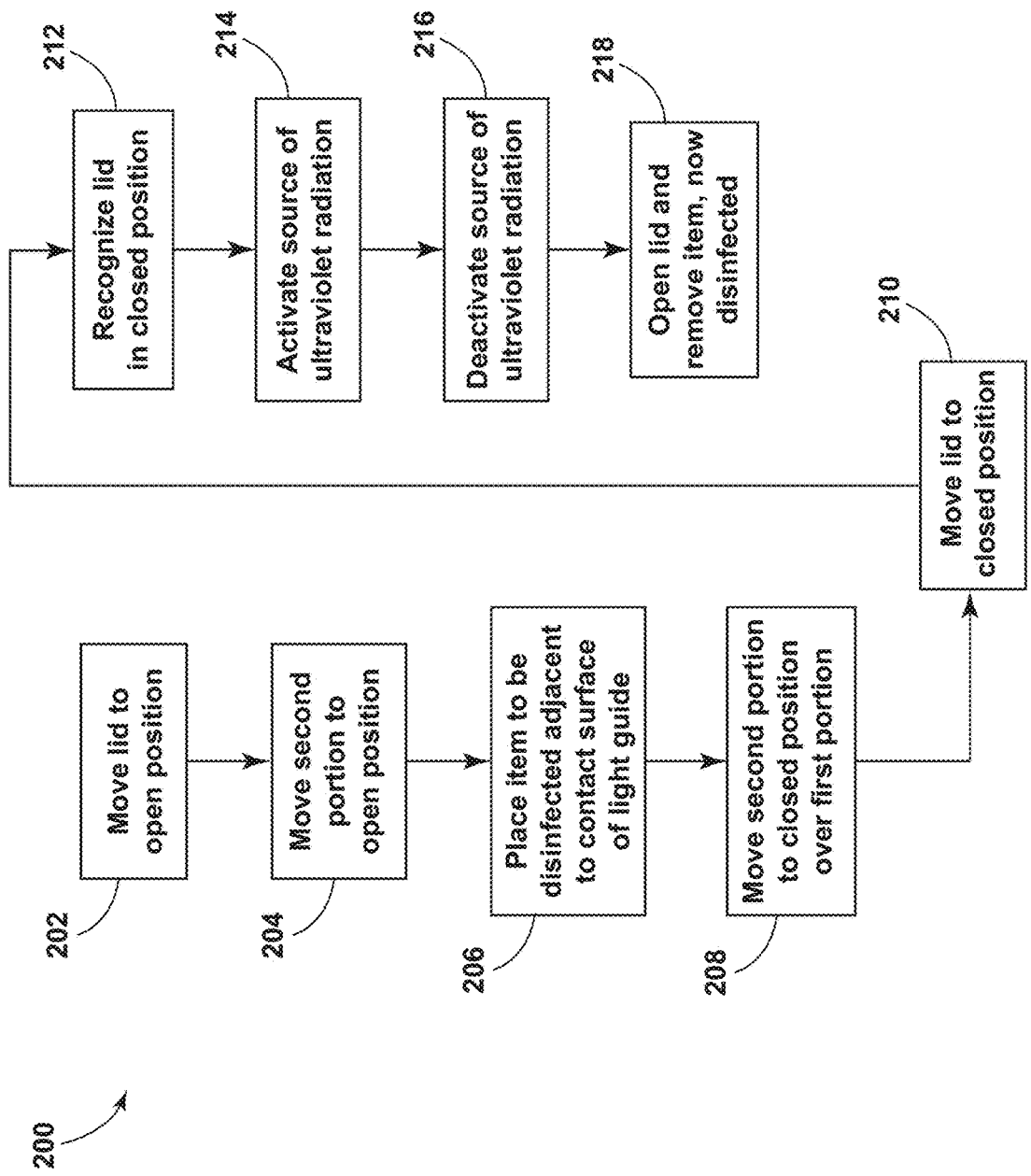
FIG. 9 is a flow diagram of an embodiment of a method of disinfecting the item with the vehicle.
Figure 10:
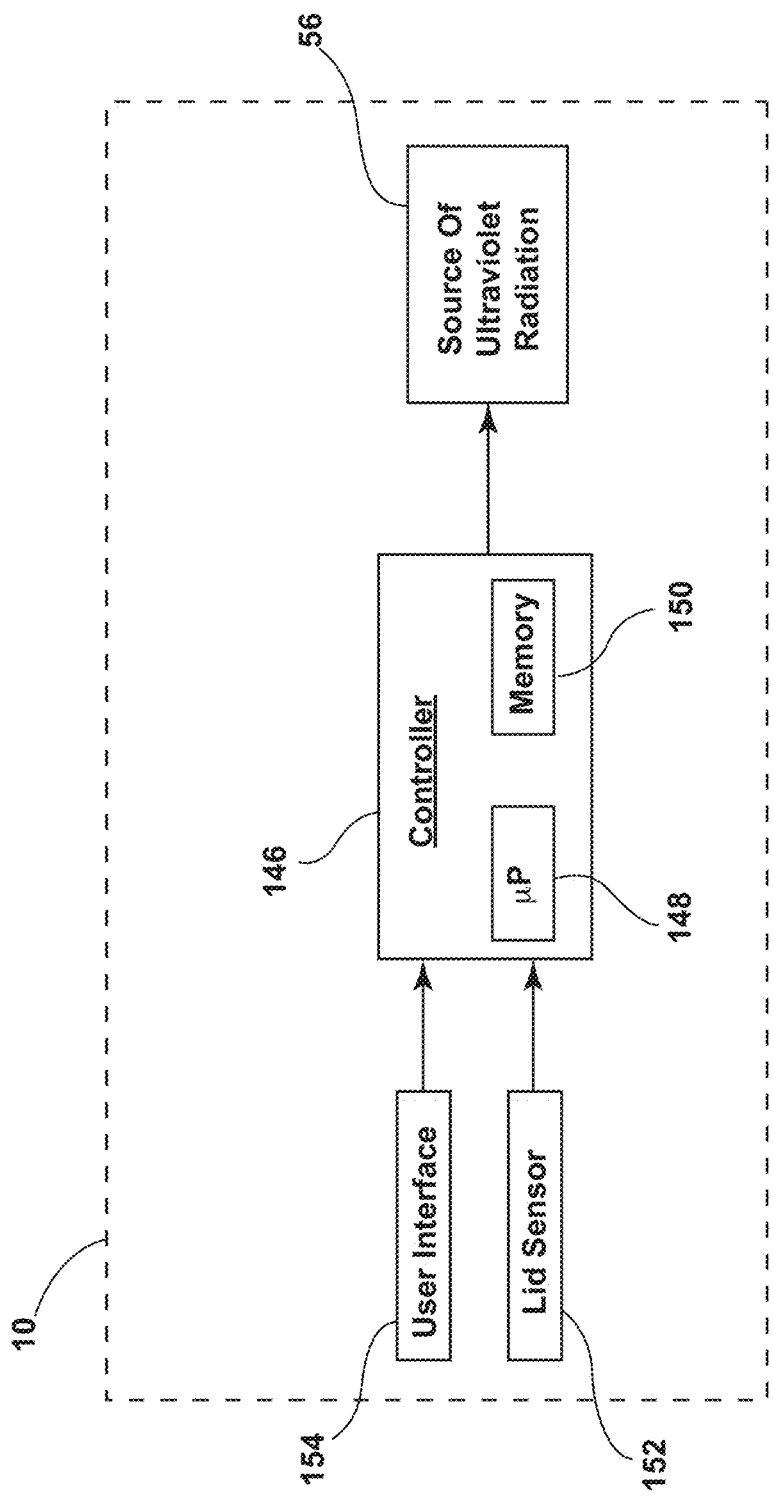
FIG. 10 is a schematic diagram of the vehicle of FIG. 1, illustrating the vehicle having a controller that controls the source of ultraviolet radiation and that receives input from a sensor to determine whether the lid is closed and a user interface.

Referring now additionally to FIGS. 9-10, a method 200 of disinfecting items within a vehicle 10 is disposed. At step 202, the method 200 includes moving the lid 60 from the closed position 62 (see FIG. 1) to the open position 64 (see FIG. 2). If the lid 60 is hingedly attached to the base 48, then moving the lid 60 from the open position 64 to the closed position 62 entails rotating the lid 60 away from the base 48. Moving the lid 60 to the open position 64 reveals the light guide 68A₁, or the light guide 68B. If the light guide 68B is utilized, then the method 200 includes, at step 204, moving the second portion 104 of the light guide 68B to the open position 132. This can be achieved by lifting or otherwise manipulating the second portion 104 away from the first portion 102. The second portion 104 can be placed over the lid 60, such as over the second reflective layer 140, as illustrated in FIG. 3B. In any event, moving the second portion 104 away from the first portion 102 reveals the contact surface 108 of the first portion 102.

The method 200 further includes, at step 206, placing the item 46 to be disinfected adjacent to the contact surface 78 of the light guide 68A₁, or the contact surface 108 of the first portion 102 of the light guide 68B. In the illustrated embodiments, the item 46 is a smart phone. However, the item 46 could be anything that fits, such as a pacifier, a wallet, headphones, hard currency, and so on. If the light guide 68B with the second portion 104 is utilized, then the method 200, at step 208, further includes manipulating the second portion 104 to the closed position 134 over the first portion 102.

The method 200 further includes, at step 210, manipulating the lid 60 to the closed position 62. When the lid 60 is in the closed position 62, the contact surface 78 of the light guide 68A₁ and the contact surface 88 of the second light guide 68A₂ both contact the item 46. The compressive layer 142 and the second compressive layer 144 force the contact surface 78 of the light guide 68A₁ and the contact surface 88 of the second light guide 68A₂ to compress against the item 46 and, if there are no other items interfering, to essentially seal around the item 46. The side surface 98c of the second light guide 68A₂ abuts against the sources 56 of ultraviolet radiation 58 at the side surface 54c of the base 48.

Alternatively, if the light guide 68B is utilized, the contact surface 108 of the first portion 102 and the contact surface 120 of the second portion 104 both contact the item 46. The compressive layer 142 and the second compressive layer 144 force the contact surface 108 of the first portion 102 and the contact surface 120 of the second portion 104 to compress against the item 46, and, if there is no other item interfering, to essentially seal around the item 46. In either embodiment, molded silicon is flexible and conforms well to the shape of the item 46. As in embodiments illustrated at FIGS. 7A and 7B, the compressive layer 142 below the item 46 and the second compressive layer 144 above the item 46 force the light guide 68A₁ and second light guide 68A₂, or the first portion 102 and the second portion 104 of the light guide 68B, as the case may be, to contact the item 46 from above and below the item 46 and conform to the item 46. The lid 60 cooperates with the base 48 to seal the interior chamber 50.

In embodiments, at step 212, the method 200 further includes recognizing that the lid 60 is in the closed position 62. The vehicle 10 further includes a controller 146. The controller 146 includes a microprocessor 148 and memory 150. The microprocessor 148 executes one or more programs stored in the memory 150. The vehicle 10 further includes a sensor 152 that senses whether the lid 60 is in the closed position 62. The sensor 152 is in communication with the controller 146. The sensor 152 could be a capacitive sensor disposed at the lid 60 that provides a signal when the lid 60 is in the closed position 62 that the controller 146 interprets as the lid 60 being in the closed position 62.

The method 200, at step 214, further includes activating the source 56 of ultraviolet radiation 58 to emit ultraviolet radiation 58. The controller 146 is in communication with the source 56 of ultraviolet radiation 58 and can activate or deactivate the source 56. In embodiments, the controller 146 activates the source 56 of ultraviolet radiation 58 whenever the controller 146 senses that the lid 60 has moved from the open position 64 to the closed position 62. In other embodiments, the vehicle 10 further includes a user interface 154, and the controller 146 activates the source 56 of ultraviolet radiation 58 whenever the controller 146 receives input from the user interface 154 commanding activation of the source 56 of ultraviolet radiation 58. If the controller 146 senses that the lid 60 is not in the closed position 62, the controller 146 does not activate the source 56 of ultraviolet radiation 58 and provides notification at the user interface 154 (such as at a display screen 156) that the lid 60 is not in the closed position 62. Once the lid 60 is manipulated to the closed position 62, and the sensor 152 provides the controller 146 with the requisite input, then the controller 146 activates the source 56 of ultraviolet radiation 58. The controller 146 can activate some other light source (such as a visible red LED) at the disinfection apparatus 28 to indicate that the controller 146 has activated the source 56 of ultraviolet radiation 58.

The source 56 of ultraviolet radiation 58 emits ultraviolet radiation 58 into the housing 44 of the disinfection apparatus 28. The ultraviolet radiation 58 disinfects the item 46 disposed in the housing 44. More particularly, with the embodiment of the light guide 68A₁, the ultraviolet radiation 58 that the source 56 of ultraviolet radiation 58 emits enters the light guide 68A₁ through the side surface 72c and the second light guide 68A₂ through the side surface 98c. The ultraviolet radiation 58 is guided throughout the interior chamber 50 via internal reflection within the light guide 68A₁ and the second light guide 68A₂, and the ultraviolet radiation 58 exits out of the light guide 68A₁ through the contact surface 78 (such as through projections 82 and/or recesses 84 at the contact surface 78) and out of the second light guide 68A₂ through the contact surface 88 (such as through projections 82 and/or recesses 84 at the contact surface 88). A portion of the ultraviolet radiation 58 exiting out of the contact surfaces 78, 88 irradiates the item 46. Because the compressive layer 142 and the second compressive layer 144 force the contact surfaces 78, 88 close to the item 46, the ultraviolet radiation 58 impinging upon the item 46 has a higher intensity leading to a disinfection period of time than if the compressive layer 142 and the second compressive layer 144 did not do so. After a period of time, the irradiation of the ultraviolet radiation 58 upon the item 46 disinfects the item 46. The reflective layer 138 and the second reflective layer 140 help reflect ultraviolet radiation 58 back within the light guide 68A₁ and the second light guide 68A₂, decreasing the amount of ultraviolet radiation 58 that the housing 44 absorbs.

With the embodiment of the light guide 68B, the ultraviolet radiation 58 enters both the first portion 102 and the second portion 104 of the light guide 68B through the side surface 114c at the binding portion 100. The ultraviolet radiation 58 is guided throughout the interior chamber 50 via internal reflection within the first portion 102 and the second portion 104, and the ultraviolet radiation 58 exits out of the first portion 102 through the contact surface 108 (such as through projections 82 and/or recesses 84 at the contact surface 108) and out of the second portion 104 through the contact surface 120 (such as through projections 82 and/or recesses 84 at the contact surface 120). A portion of the ultraviolet radiation 58 exiting out of the contact surfaces 108, 120 irradiates the item 46. The reflective layer 138 and the second reflective layer 140 help reflect ultraviolet radiation 58 back within the first portion 102 and the second portion 104 of the light guide 68B, increasing efficiency as mentioned. The compressive layer 142 and the second compressive layer 144 increase efficiency as well, as described above.

The method 200 further includes, at step 216, deactivating the source 56 of ultraviolet radiation 58. After a period of time, the irradiation of the ultraviolet radiation 58 upon the item 46 disinfects the item 46. The controller 146 can count the time after the controller 146 activated the source 56 of ultraviolet radiation 58. The controller 146 can deactivate the source 56 of ultraviolet radiation 58 after a predetermined period of time. An occupant of the vehicle 10 can set the predetermined period of time at the user interface 154, which the controller 146 accepts as input, and deactivates the source 56 of ultraviolet radiation 58 after the set period of time. The controller 146 can deactivate the source 56 of ultraviolet radiation 58 upon receiving input from the sensor 152 that the lid 60 is no longer in the closed position 62. The lid 60 being in the closed position 62 lowers, minimizes, or prevents leakage of ultraviolet radiation 58 from the housing 44 to the interior 12 of the vehicle 10. The controller 146 can activate some other light source (such as a visible green LED) at the disinfection apparatus 28 to indicate that the controller 146 has deactivated the source 56 of ultraviolet radiation 58.

The method 200 further includes, at step 218, opening the lid 60 and removing the item 46. If the light guide 68B is utilized, this step further entails moving the second portion 104 to the open position 132. The item 46 has been disinfected.

The disinfection apparatus 28 provides many advantages, including occupying little space in the interior 12 of the vehicle 10. The compressive layer 142 and the second compressive layer 144 prevent the item 46 from moving while in the housing 44 and thus prevent noise generation. The emission of the ultraviolet radiation 58 to disinfect the item 46 takes a short period of time, such as less than five minutes, less than four minutes, less than three minutes, less than two minutes, and even less than one minute. Further, if the light guide 68A$_1$, the second light guide 68A$_2$, or the light guide 68B are made from silicone, then they are easily cleanable.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is to be understood that variations and modifications can be made on the aforementioned structure without departing from the concepts of the present invention, and further it is to be understood that such concepts are intended to be covered by the following claims unless these claims by their language expressly state otherwise.

What is claimed is:

1. A disinfection apparatus for a vehicle comprising:
    a housing to accept an item to be disinfected, the housing comprising (i) a base including a primary surface and a side surface extending at least approximately orthogonally from the primary surface, the primary surface and side surface forming an interior chamber; (ii) a lid operably connected to the base, the lid manipulable to, from, and between a closed position where the lid covers the interior chamber and an open position where the lid does not cover the interior chamber; (iii) a first light guide disposed at the base, the first light guide comprising a contact surface to contact the item to be disinfected, an opposite surface disposed over the primary surface of the base, and a side surface at least approximately orthogonal to the contact surface that is disposed proximate the side surface of the base; and (iv) a second light guide attached to the lid, the second light guide comprising a contact surface that faces the contact surface of the first light guide and contacts the item to be disinfected when the lid is in the closed position but is separated from the contact surface of the first light guide when the lid is in the open position, and a side surface at least approximately orthogonal to the contact surface; and
    a source of ultraviolet radiation configured to emit ultraviolet radiation into the housing from the side surface of the base, the source of ultraviolet radiation abutting the side surface of the first light guide and the side surface of the second light guide, when the lid is in the closed position, such that a portion of the ultraviolet radiation that the source of ultraviolet radiation emits transmits (i) through the side surface of the first light guide to reflect internally within the first light guide and then transmits through the contact surface of the first light guide and onto the item and (ii) through the side surface of the second light guide to reflect internally within the second light guide and then transmits through the contact surface of the second light guide and onto the item.

2. The disinfection apparatus of claim 1,
    wherein, the first light guide and the second light guide comprise silicone.

3. The disinfection apparatus of claim 1,
    the source of ultraviolet radiation is a light emitting diode configured to emit electromagnetic radiation having a peak intensity within a wavelength range of 200 nm to 300 nm.

4. The disinfection apparatus of claim 1,
    the disinfection apparatus further comprising a reflective layer, disposed adjacent to the opposite surface of the first light guide, that reflects at least 40 percent of incident electromagnetic radiation having a wavelength in a range of 200 nm to 300 nm.

5. The disinfection apparatus of claim 1,
    the disinfection apparatus further comprising a reflective layer, disposed adjacent to the second light guide, that reflects at least 40 percent of incident electromagnetic radiation having a wavelength in a range of 200 nm to 300 nm.

6. The disinfection apparatus of claim 1,
    the side surface of the second light guide does not abut the source of ultraviolet radiation when the lid is in the open position.

7. The disinfection apparatus of claim 1,
    the first light guide further comprising recesses extending into the contact surface or projections extending out of the contact surface.

8. The disinfection apparatus of claim 1 further comprising:
    a first compressive layer disposed between the base of the housing and the opposite surface of the first light guide; and
    a second compressive layer disposed between the lid of the housing and the second light guide;
    wherein, the first compressive layer and the second compressive layer compress the contact surface of the first light guide against the contact surface of the second light guide, when the lid is in the closed position.

9. The disinfection apparatus of claim 1,
the first light guide is visually transparent; and
a portion of the opposite surface of the first light guide is separable from the primary surface of the base.

10. The disinfection apparatus of claim 1,
wherein, the first light guide comprises a thickness that extends between the contact surface and the opposite surface, and the thickness decreases as a function of a distance from the side surface of the first light guide that abuts the source of ultraviolet radiation.

11. A disinfection apparatus for a vehicle comprising:
a housing comprising a base forming an interior chamber to accept an item to be disinfected;
a source of ultraviolet radiation configured to emit ultraviolet radiation into the housing; and
a light guide disposed within the interior chamber and accepting ultraviolet radiation from the source of ultraviolet radiation within the interior chamber, the light guide comprising a first portion, a second portion, and a binding portion connecting the first portion and the second portion, wherein the first portion comprises a contact surface to contact the item to be disinfected, the second portion comprises a contact surface to contact the item to be disinfected, the second portion has an open position relative to the first portion in which the contact surface of the second portion is separated from the contact surface of the first portion, and the second portion has a closed position relative to the first portion in which the contact surface of the second portion is disposed adjacent the contact surface of the first portion.

12. The disinfection apparatus of claim 11,
the housing further comprising:
a lid operably connected to the base, the lid manipulable to, from, and between a closed position where the lid covers the interior chamber and an open position where the lid does not cover the interior chamber.

13. The disinfection apparatus of claim 11,
the source of ultraviolet radiation is a light emitting diode configured to emit electromagnetic radiation having a peak intensity within a wavelength range of 200 nm to 300 nm.

14. The disinfection apparatus of claim 11,
the first portion of the light guide further comprising an opposite surface that faces in a generally opposite direction as the contact surface of the first portion; and
the disinfection apparatus further comprising a reflective layer, disposed adjacent to the opposite surface of the first portion of the light guide, that reflects at least 40 percent of incident electromagnetic radiation having a wavelength in a range of 200 nm to 300 nm.

15. The disinfection apparatus of claim 12,
the second portion of the light guide further comprising an opposite surface that faces in a generally opposite direction as the contact surface of the second portion; and
the disinfection apparatus further comprising a second reflective layer disposed at the lid that abuts the opposite surface of the second portion of the light guide when the second portion of the light guide is in the closed position and the lid is in the closed position.

16. The disinfection apparatus of claim 11,
the base comprises a primary surface and a side surface extending at least approximately orthogonally from the primary surface, the primary surface and the side surface forming the interior chamber;
the light guide further comprises a side surface at the binding portion that abuts the source of ultraviolet radiation; and
the source of ultraviolet radiation emits the ultraviolet radiation from the side surface of the base through the side surface of the light guide at the binding portion and into both the first portion and the second portion of the light guide.

17. The disinfection apparatus of claim 12,
the first portion of the light guide further comprising an opposite surface that faces in a generally opposite direction as the contact surface of the first portion;
the second portion of the light guide further comprising an opposite surface that faces in a generally opposite direction as the contact surface of the second portion; and
the disinfection apparatus further comprising:
a first compressive layer disposed between the base of the housing and the opposite surface of the first portion of the light guide; and
a second compressive layer attached to the lid that is disposed between the lid and the opposite surface of the second portion of the light guide when the second portion of the light guide is in the closed position and the lid is in the closed position;
the first compressive layer and the second compressive layer compress the contact surface of the first portion of the light guide against the contact surface of second portion of the light guide, when the lid is in the closed position.

18. The disinfection apparatus of claim 11,
the first portion of the light guide further comprising an opposite surface that faces in a generally opposite direction as the contact surface of the first portion;
the light guide is visually transparent; and
the light guide is attached to the base, but a portion of the opposite surface of the first portion of the light guide is separable from the base.

19. The disinfection apparatus of claim 11,
the first portion of the light guide further comprising an opposite surface that faces in a generally opposite direction as the contact surface of the first portion, and a thickness from the opposite surface to the contact surface;
the second portion of the light guide further comprising an opposite surface that faces in a generally opposite direction as the contact surface of the second portion, and a thickness from the opposite surface to the contact surface; and
both the thickness of the first portion and the thickness of the second portion of the light guide decrease as a function of a distance from the binding portion.

20. A method of disinfecting an item with a vehicle comprising:
activating a source of ultraviolet radiation to emit ultraviolet radiation into a light guide disposed within a housing of a disinfection apparatus to disinfect an item disposed in the housing;
wherein, the light guide comprises (i) a first portion comprising a contact surface on which the item is placed, (ii) a second portion, in a closed position, comprising a contact surface that together the with the contact surface of the first portion sandwiches the item, and (iii) a binding portion connecting the first portion and the second portion, the binding portion directing the ultraviolet radiation into the first portion and the second portion;

wherein, the second portion is configured to have an open position relative to the first portion, such that the contact surface of the first portion and the contact surface of the second portion are closer together in the closed position compared to the open position; and wherein, the ultraviolet radiation is emitted through the contact surfaces of the first portion and the second portion and onto the item.

* * * * *